(12) United States Patent
Gaydos et al.

(10) Patent No.: US 7,959,609 B2
(45) Date of Patent: Jun. 14, 2011

(54) ACCURATE METERING SYSTEM

(75) Inventors: Peter A. Gaydos, Hilliard, OH (US);
Brian A. Lipp, Columbus, OH (US);
Bruce D. Mcveety, Dublin, OH (US);
George C. Proicou, Gahanna, OH (US)

(73) Assignee: Battelle Memorial Institute, Columbus, OH (US)

( * ) Notice: Subject to any disclaimer, the term of this patent is extended or adjusted under 35 U.S.C. 154(b) by 946 days.

(21) Appl. No.: 11/560,540

(22) Filed: Nov. 16, 2006

(65) Prior Publication Data
US 2008/0308580 A1    Dec. 18, 2008

Related U.S. Application Data

(60) Provisional application No. 60/773,272, filed on Feb. 14, 2006.

(51) Int. Cl.
*A61M 37/00* (2006.01)
(52) U.S. Cl. ....................................... 604/155
(58) Field of Classification Search ............ 604/152, 604/154, 155, 207–211, 218, 222, 224, 228–230, 604/890.1
See application file for complete search history.

(56) References Cited

U.S. PATENT DOCUMENTS

| | | | |
|---|---|---|---|
| 4,529,401 A * | 7/1985 | Leslie et al. | 604/131 |
| 6,003,736 A | 12/1999 | Ljunggren | 222/309 |
| 6,263,778 B1 * | 7/2001 | Brass et al. | 92/32 |
| 6,286,725 B1 | 9/2001 | Gerber | 222/207 |
| 6,368,314 B1 | 4/2002 | Kipfer et al. | |
| 6,423,035 B1 * | 7/2002 | Das et al. | 604/155 |
| 6,648,605 B2 | 11/2003 | Nelson | 417/53 |
| 6,663,602 B2 | 12/2003 | Møller | 604/211 |
| 6,761,286 B2 | 7/2004 | Py et al. | 222/105 |
| 6,770,054 B1 * | 8/2004 | Smolyarov et al. | 604/140 |
| 6,835,194 B2 * | 12/2004 | Johnson et al. | 604/131 |
| 6,957,752 B2 | 10/2005 | Py et al. | 222/390 |
| 6,997,906 B2 | 2/2006 | Langley et al. | |
| 2002/0165491 A1 * | 11/2002 | Reilly | 604/154 |

FOREIGN PATENT DOCUMENTS

| | | |
|---|---|---|
| WO | WO 00/38770 | 7/2000 |
| WO | WO 01/37903 | 5/2001 |

OTHER PUBLICATIONS

U.S. Appl. No. 60/773,239, filed Feb. 14, 2006, Trees et al.

* cited by examiner

*Primary Examiner* — Nicholas D Lucchesi
*Assistant Examiner* — Nathan R Price
(74) *Attorney, Agent, or Firm* — Frost Brown Todd LLC

(57) ABSTRACT

The present invention is directed to metering devices, systems, and methods that mitigate differential thermal expansion/contraction for the efficient, accurate, and reproducible metered delivery of fluids. The present invention allows the net fluid volume and a plunger location within a fluid dispensing container to automatically adjust under the influence of differential thermal expansion/contraction between the fluid and the fluid dispensing container that the fluid is contained within. Further, the present invention allows the metering system drive to sense the adjusted plunger location and allows the metering system drive to re-zero itself to produce an accurate volumetric delivery of fluid from the fluid dispensing container. The metering system includes means for controlling the travel of the metering system drive, and hence the travel of the plunger into the fluid dispensing container, for delivering accurate/precise amounts of the fluid from the fluid dispensing container. The metering system may also mitigate dead volume in the metering system.

53 Claims, 17 Drawing Sheets

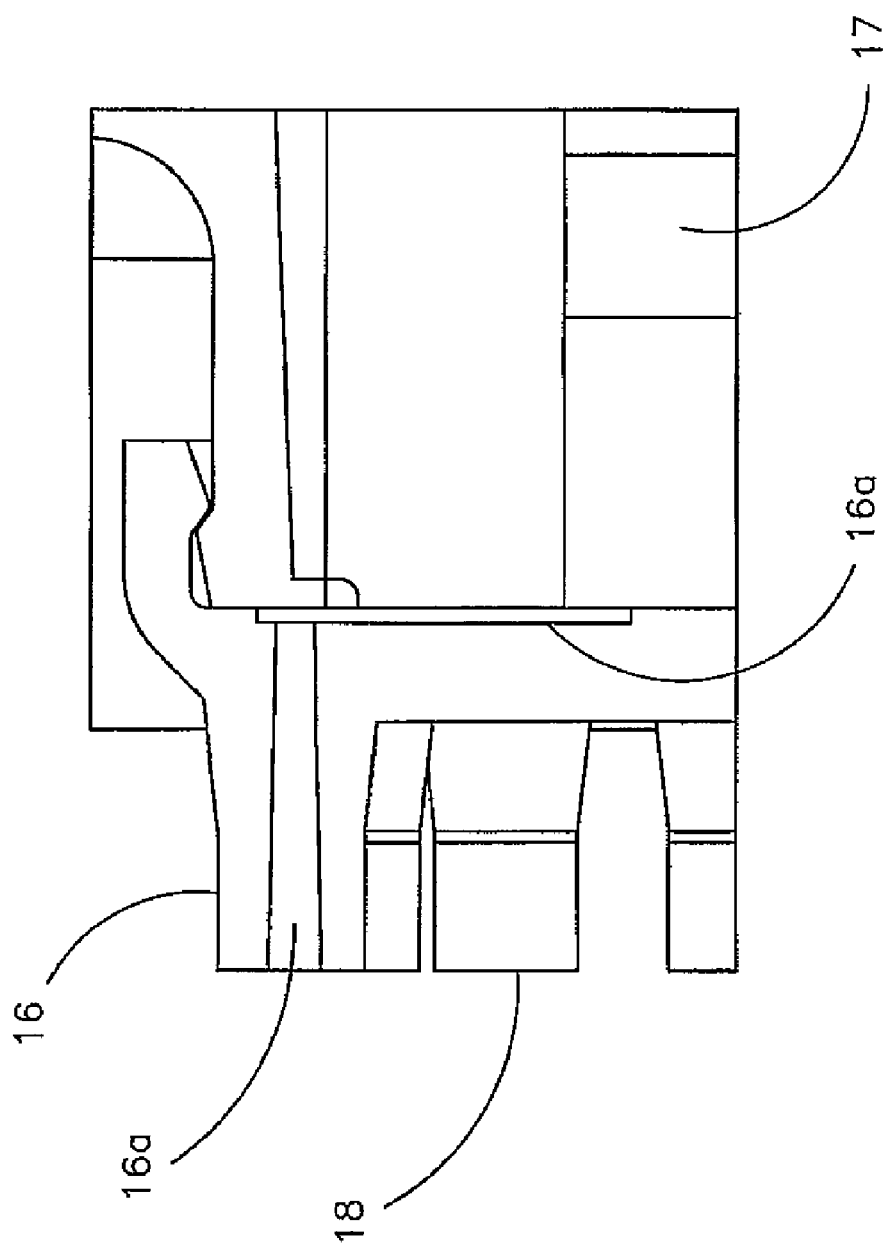

① + ④ ACTIVE—MOTOR DRIVES FORWARD

① + ⑤ ACTIVE—MOTOR DRIVES FORWARD AT HIGH SPEED

② + ③ ACTIVE—MOTOR REVERSES AT HIGH SPEED

ACCURATE METERING SYSTEM

CROSS REFERENCE TO RELATED APPLICATIONS

The subject matter disclosed herein claims priority under 35 U.S.C. §119(e) to provisional U.S. Patent Application Ser. No. 60/773,272, filed Feb. 14, 2006, entitled "ACCURATE METERING SYSTEM," which is assigned to the assignee of the present application and hereby incorporated herein by reference in its entirety.

The subject matter disclosed herein is related to the subject matter disclosed in the following commonly assigned application: U.S. Provisional Patent Application No. 60/773,239, filed on Feb. 14, 2006, and entitled "DISSOCIATED DISCHARGE EHD SPRAYER WITH ELECTRIC FIELD SHIELD," the entirety of said application is hereby incorporated by reference herein.

TECHNOLOGY FIELD

The subject matter described herein relates generally to metering systems, and in particular to an accurate metering system that mitigates the effects of differential thermal expansion/contraction between a fluid and a container for the controlled delivery of flowable materials, such as liquids, solutions, dispersions, suspensions, gels, pastes, and other fluids.

BACKGROUND

Treating disease by inhaling medicines has been around for centuries but has advanced and grown considerably since the mid-20th century. Using inhalation therapy to deliver both topically and systemically active drug compounds is increasing as the health-care community recognizes the benefits this route of administration offers to patients. In order for inhalation treatments to be effective, pulmonary delivery devices must enable efficient, safe and consistent delivery of drugs to and through the lungs.

Syringe-based metering systems are well-known in the art of metering systems for their accuracy and simplicity. In a metering system having a rigid syringe/vial system with little or no compressible head space, however, differential thermal expansion and/or contraction can cause net volume change of the fluid contained in the syringe or vial (i.e., a different expansion or contraction between the fluid and the rigid syringe). This volume expansion and/or contraction must be accommodated in the syringe/vial to prevent either an expanding fluid volume from being expressed from the syringe, or a contracting volume from allowing outside air to enter the vial, or creating a low enough vial pressure to cause out-gassing of air or a vapor phase of the liquid in the vial. These volumetric changes can adversely impact metering accuracy.

In addition, metering systems having valves and/or nozzles located downstream of a fluid container outlet typically experience problems with dead volume in the space or passageways fluidly connecting the container outlet and the valves/nozzles. This dead volume can lead to inaccurate and/or inconsistent delivery of fluids. Metering systems having dead volume can be manually primed by the user prior to delivery, however, this requires an extra step for the user. Also, in such manual priming systems, the user may not properly prime the metering system prior to use leading to inaccuracies in fluid delivery.

What is needed are devices, systems, and methods that account for differential thermal expansion/contraction and/or account for dead volume in a metering system to ensure efficient, accurate, and reproducible metered delivery of fluids.

SUMMARY

In view of the above shortcomings and drawbacks, devices, systems, and methods for the mitigation of differential thermal expansion/contraction in a metering system are provided. Also provided are devices, systems, and methods for the mitigation of problems associated with priming dead volume in a metering system. The devices, systems, and methods provide for the efficient, accurate, and reproducible metered delivery of fluids. This technology is particularly well-suited for, but by no means limited to, syringe-based metering systems.

According to one embodiment of the present invention, an accurate metering device is provided. The accurate metering system includes a fluid dispensing container containing a fluid to be dispensed, wherein the fluid dispensing container comprises a reducible volume. The system includes a movable portion that is free to move in response to changes in fluid volume of the fluid contained within the fluid dispensing container. A net fluid volume is defined by the fluid dispensing container and movable portion, wherein the net fluid volume within the fluid dispensing container changes as the movable portion moves with respect to the fluid dispensing container. A metering drive is provided to selectively contact the movable portion. A starting point comprises a point wherein the metering drive is re-zeroed. The starting point may include a point where the metering drive engages the movable portion of the fluid dispensing container, becomes loaded, commences fluid delivery, etc. The metering drive may be actuated a known amount from the starting point thus moving the movable portion and reducing the reducible volume of the fluid dispensing container and causing a specific quantity of the fluid to be dispensed from the fluid dispensing container.

According to another embodiment of the invention, a syringe-based metering system that mitigates differential thermal expansion/contraction is provided. The syringe-based metering system includes a syringe defining an interior volume for containing a fluid. The syringe includes an outlet opening at a front end of the syringe. A piston-type plunger is slidably disposed within the syringe through an opening in a rear end of the syringe. A net fluid volume is defined by a location of the plunger within the syringe. The net fluid volume changes with movement of the plunger within the syringe. A metering drive can selectively engage and disengage the plunger, wherein the metering drive engages the plunger through the opening in the rear end of the syringe and is advanced to expel fluid from the syringe. The metering drive disengages the plunger by being backed off of the plunger when the syringe-based metering system is not in use. The plunger is permitted to slide axially within the syringe to mitigate differential thermal expansion and/or contraction between the syringe and the fluid contained within the syringe.

According to another embodiment of the invention, a method of mitigating the effects of differential thermal expansion/contraction in a metering system is provided to ensure accurate metering of a fluid. The method includes containing a fluid to be dispensed in a fluid dispensing container having a reducible volume. Providing a movable portion that can slide within the fluid dispensing container to reduce the reducible volume causing the fluid to be dispensed. Providing a metering drive that can selectively engage the movable portion to move the movable portion causing the reducible volume of the fluid dispensing container to be reduced in an operating mode. Mitigating the effects of differential thermal expansion by allowing the metering drive to be backed off of the movable portion in a non-operating mode to provide a clearance between the movable portion and the metering drive.

According to another aspect of the invention, the system and methods include mitigating the effect of differential thermal expansion and/or contraction between the fluid dispensing container and the fluid contained within the fluid dispensing container by allowing the movable portion to move back and forth in response to an expanding and/or contracting fluid volume of the fluid contained within the fluid dispensing container caused by an increasing and/or decreasing temperature.

According to another aspect of the invention, the system and methods include mitigating the effect of differential thermal contraction between the fluid dispensing container and the fluid contained within the fluid dispensing container by allowing the movable portion to move forward in response to a contracting fluid volume of the fluid contained within the fluid dispensing container caused by a changing (e.g., generally decreasing) temperature.

According to another aspect of the invention, the system and methods include mitigating the effect of differential thermal expansion between the fluid dispensing container and the fluid contained within the fluid dispensing container by allowing the movable portion to move backward in response to an expanding fluid volume of the fluid contained within the fluid dispensing container caused by a changing (e.g., generally increasing) temperature.

According to another aspect of the invention, the system and methods include seeking the movable portion with the metering drive and sensing engagement of the metering drive with the movable portion. Designating a starting point for metering of the fluid when the engagement of the metering drive with the movable portion is sensed and metering a dose of fluid from the starting point.

According to another aspect of the invention, the system and methods include filling a nozzle dead volume with fluid during the step of seeking and before designation of the starting point.

According to another aspect of the invention, the system and methods include sensing a movement of the metering drive and correlating movement of the metering drive to the set volume of fluid to deliver a set volume of fluid from the fluid dispensing container.

According to another aspect of the invention, the system and methods include engaging an encoder disk with a gear train, driving the metering drive and counting one or more windows in the encoder disk. Each of the one or more windows represents a set volume of fluid.

According to another aspect of the invention, the system and methods include providing an interference fit between the movable portion and the fluid dispensing container, wherein the interference fit creates a friction force between the movable portion and the fluid dispensing container. In one embodiment, the systems and methods may include designing the metering system to have a differential thermal expansion sliding force, which is the force required to cause the movable portion to slide rearward within the fluid dispensing container in response to an increasing temperature. Preferably, the differential thermal expansion sliding force is greater than the friction force between the movable portion and the fluid dispensing container. More preferably, the differential thermal expansion sliding force is also less than the cracking pressure of any outlet valve. In another embodiment, the system and methods may include designing the metering system to have a differential thermal contraction sliding force, which is the force required to cause the movable portion to slide forward within the fluid dispensing container in response to a decreasing temperature. Preferably, the differential thermal contraction sliding force is greater than the friction force between the movable portion and the fluid dispensing container.

According to another aspect of the invention, the system and methods include designing a metering system to have an actuation sliding force required to cause the movable portion to slide within the fluid dispensing container when the metering system is actuated. The actuation sliding force being greater than the friction force between the movable portion and the fluid dispensing container.

According to another aspect of the invention, the system and methods include providing an interference fit between the movable portion and the fluid dispensing container and sealing the fluid within the fluid dispensing container using the interference fit. The method may further include sealing an interface between the movable portion and the fluid dispensing container.

Additional features and advantages of the invention will be made apparent from the following detailed description of illustrative embodiments that proceeds with reference to the accompanying drawings.

BRIEF DESCRIPTION OF THE DRAWINGS

The invention is best understood from the following detailed description when read in connection with the accompanying drawings. The following Figures show various exemplary embodiments and various features of the present invention:

FIG. 3 is a detail view of the exemplary metering system of FIG. 2A showing the nozzle dead volume;

DETAILED DESCRIPTION OF ILLUSTRATIVE EMBODIMENTS

Figure 1:
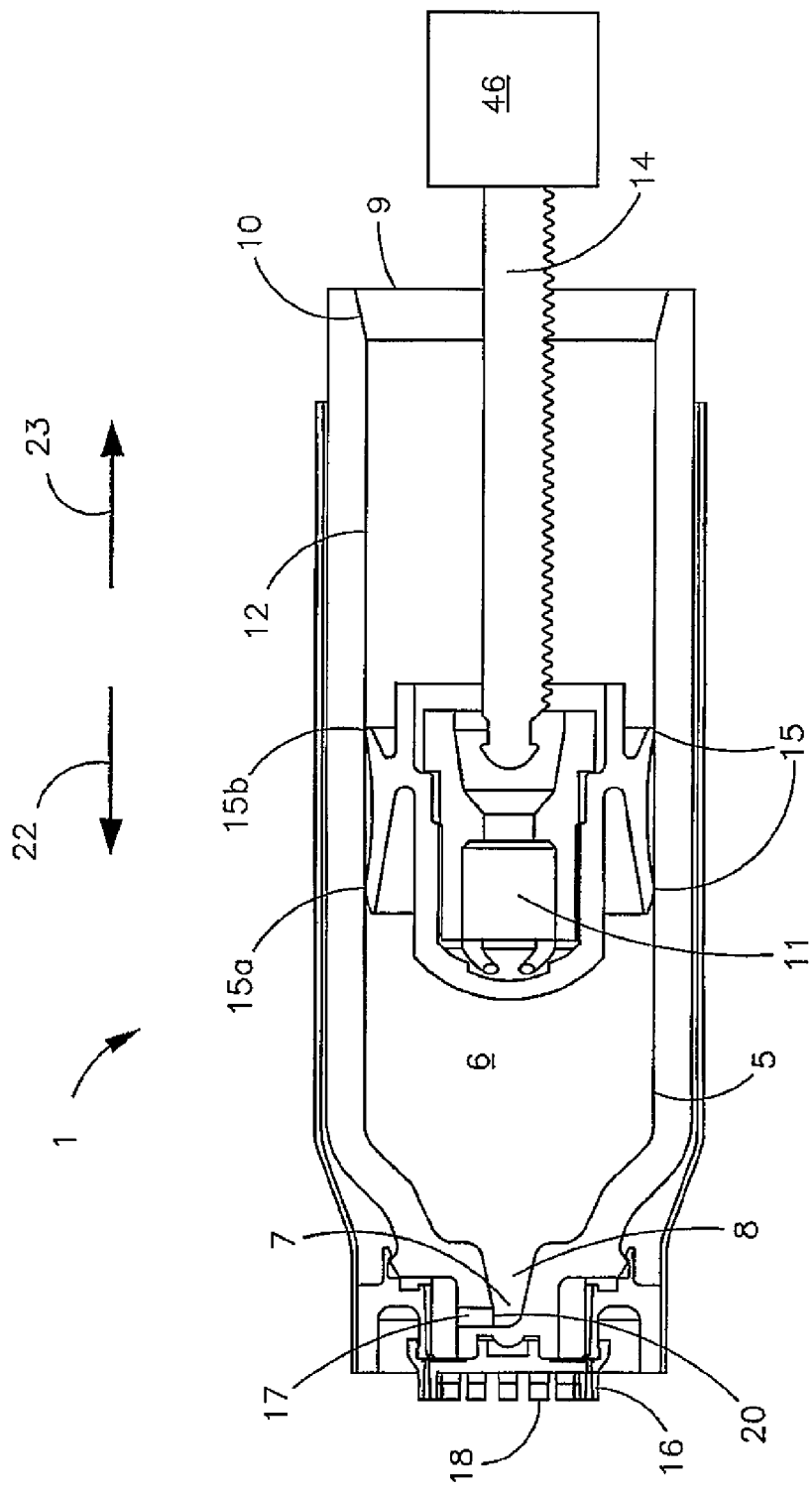
FIG. 1 is a cross-sectional view of an exemplary container and metering system for dispensing a controlled quantity of a fluid.

The present invention is directed to devices, systems, and methods for efficient, accurate, and reproducible metered delivery of fluids. Preferably, the metering system accounts for differential thermal expansion and/or contraction between a fluid dispensing container and a fluid contained within the fluid dispensing container. In addition, the metering system preferably provides for self-priming of any dead volume that may exist between the fluid dispensing container outlet and any downstream valves and/or nozzles. Fluids as used herein refers to any flowable materials, such as, for example, liquids, solutions, dispersions, suspensions, gels, pastes, and other fluids.

Although the following description of the illustrative embodiments is focused on exemplary pulmonary drug delivery devices having syringe-based metering systems, the invention is not limited to such devices, systems and methods. It is contemplated that the present invention for the mitigation of differential thermal expansion/contraction is applicable to any metering system and/or dispensing system for delivering controlled, metered amounts of a fluid wherein differential thermal expansion/contraction may be present. For example, it is contemplated that the present invention could also be applicable to other syringe-based metering systems and like dispensers, metering systems for the delivery of a variety of substances, such as medicaments, pharmaceuticals, cosmetics, hydraulics, oils, fuels, petroleum products, bio-agents, food products, cleaning agents, fertilizers, insecticides, and the like.

The present invention allows the net fluid volume and a plunger location within a fluid dispensing container to automatically adjust under the influence of differential thermal expansion/contraction between the fluid and the fluid dispensing container that the fluid is contained within. Further, the present invention allows the metering system drive to sense the adjusted plunger location and allows the metering system drive to re-zero itself to produce an accurate volumetric delivery of fluid from the fluid dispensing container. The metering system includes means for controlling the travel of the metering system drive, and hence the travel of the plunger into the fluid dispensing container, for delivering accurate and/or precise amounts of the fluid contained with the fluid dispensing container.

The accuracy of the metering system may be further enhanced by accounting for any thermal expansion and/or contraction of the fluid contained within the fluid dispensing container and then adjusting the dose delivery (e.g., the travel distance of the metering drive) based on an amount corresponding to the thermal expansion and/or contraction sensed by the accurate metering system. For example, in metering systems requiring extremely accurate metering of fluids, the amount of thermal expansion/contraction resulting from a temperature change of the fluid may be measured/sensed and the fluid delivery may be adjusted based on the measured/sensed amount of thermal expansion/contraction. In such an extreme accuracy embodiment, the characteristics/properties of the fluid contained within the fluid dispensing container may be used in conjunction with a measured/sensed thermal expansion/contraction condition to determine and adjust the actuation of the meter drive system and metering drive thus ensuring highly accurate delivery of fluid from the metering system. An extreme accuracy embodiment may be used with, for example, metering systems for delivering toxic fluids, powerful drugs, expensive fluids, and the like.

For example, in one embodiment of the accurate metering system, the location of the plunger in the fluid dispensing container may be determined and the plunger may be advanced using the metering drive by activating the metering drive system and completing, for example, two rotations of an encoder wheel. In an embodiment of an extreme accuracy metering system, for example, the amount of thermal expansion/contraction may be determined in addition to the plunger location and the metering of the fluid may be adjusted accordingly. In such an embodiment, if the fluid expands 10% due to an increase in temperature, and that thermal expansion correlates to a certain travel of the metering drive, then the extreme metering system may adjust the delivery to only advance the metering drive a distance that accounts for the travel distance resulting from thermal expansion.

The metering system that mitigates differential thermal expansion/contraction is applicable for single dose dispensing systems and/or multi-dose dispensing systems. With multi-dose dispensing systems, the metering system drive is preferably backed-off and not in contact (i.e., disengaged) with the plunger when the device is not in use (i.e., before the first use and after each use). The position of the plunger may move during non-use as a result of differential thermal expansion/contraction due to changes in temperature. The metering system for mitigating the effects of differential thermal expansion/contraction allows the metering system drive to seek and find the exact position of the plunger before a dose is administered. This feature helps ensure more efficient, accurate, and reproducible volumetric metered delivery of fluids.

Similarly, for single dose dispensing systems the metering system drive is preferably backed-off and not in contact with the plunger when the device is not in use (e.g., during shipping and storage). The metering system drive locates the exact position of the plunger prior to use because the position of the plunger may have moved during shipping/storage as a result of, for example, differential thermal expansion/contraction. Having the plunger withdrawn prior to use eliminates leakage due to increase fluid pressure and out-gassing or vaporization due to decrease fluid pressure. Again, locating the exact position of the plunger at start-up helps ensure more efficient, accurate, and reproducible volumetric metering.

Further, the metering system also preferably mitigates the adverse effects of delivery systems having dead volume that require priming prior to use. For example, in delivery systems having valves and/or nozzles located downstream of the fluid dispensing container outlet, there may be dead volume in the space or fluid passageway between the fluid dispensing container outlet and any downstream valve(s) and/or nozzle(s). A metering system having a smart metering drive system can provide fine control fluid delivery of the fluid from the fluid dispensing container up to the valve and/or nozzle thus self-priming the device by filling the dead volume prior to overcoming the cracking pressure of the valve and commencement of delivery of the metered dose.

Figure 2A:
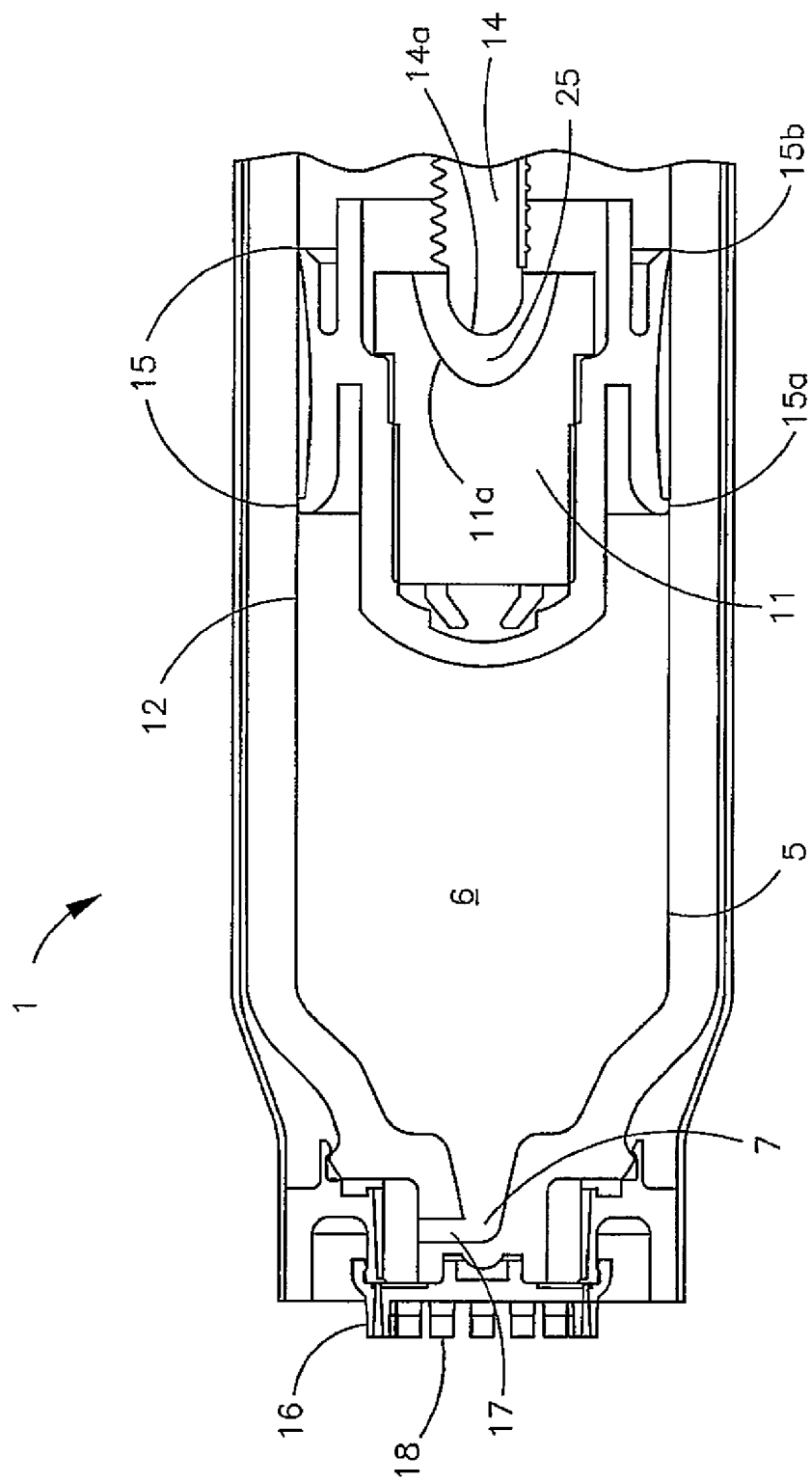
FIG. 2A is a cross-sectional view of an exemplary metering system with the metering drive disengaged.
Figure 2B:
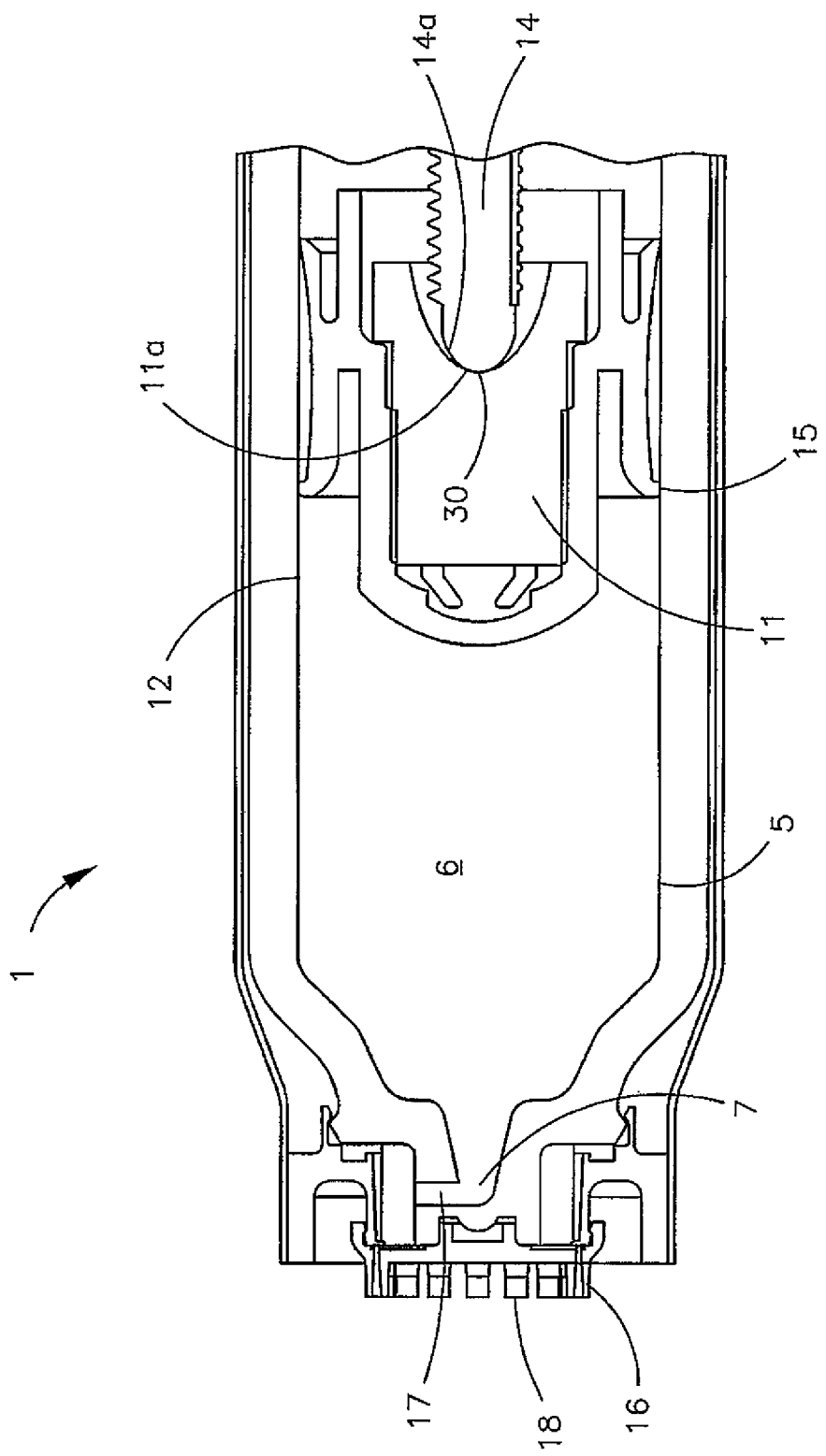
FIG. 2B is a cross-sectional view of the exemplary metering system of FIG. 2A with the metering drive engaged.

FIGS. 1, 2A, and 2B show embodiments of a syringe-based metering system 1 having a fluid dispensing container 5 defining a volume for containing a fluid 6. Fluid dispensing container as used herein refers to any contained space for holding a volume of fluid, such as, for example, a vial, a container, a syringe, a pouch, etc. Preferably, the fluid dispensing container 5 is volumetrically reducible. The fluid dispensing container includes an outlet opening 7 for allowing the fluid 6 contained within the fluid dispensing container 5 to be expelled from the fluid dispensing container 5. As shown, the outlet opening 7 may be located in a forward end 8 of the fluid dispensing container 5.

The fluid dispensing container 5 also includes a mechanism for allowing the volume of the fluid dispensing container 5 to be reduced. As shown in FIGS. 1, 2A and 2B, the fluid dispensing container 5 can include an opening 9 at a rear end 10. A plunger 111 may be slidably disposed within the fluid dispensing container 5 such that the plunger 11 can slide relative to a sidewall 12 of the fluid dispensing container 5. Plunger, as used herein, refers to a movable portion of the fluid dispensing container used to reduce the volume of the fluid dispensing container, such as, for example, a plunger, a piston-type plunger, a collapsible side-wall(s), etc. As the plunger 11 moves forward, the volume of the fluid dispensing container 5 for holding the fluid 6 is reduced. In the illustrated embodiments, the sidewall 12 of the fluid dispensing container 5 is rigid and does not move as the plunger 11 slides within the vial sidewall 12. Also, the sidewall 12 of the fluid dispensing container 5 is preferably rigid. The fluid dispensing container 5 and plunger 11 have corresponding shapes, and in a preferred embodiment the fluid dispensing container 5 and the plunger 11 include a generally cylindrical shape.

As shown in FIGS. 1, 2A, 2B, 5 and 6, the metering system 1 may also include a metering drive system 46. A smart and/or intelligent metering drive system 46 as used herein is a system that is capable of determining the location of the movable portion 11 of the fluid dispensing container 5 prior to commencement of dispensing of fluid from the fluid dispensing container 5. In addition, a smart and/or intelligent metering drive system 46 preferably allows a metering drive 14 to be disengaged from the movable portion 11 when the device is not in use thus allowing the movable portion 11 to slide freely in the fluid dispensing container 5 in response to changes in temperature. Metering drive, as used herein, refers to any mechanism for engaging and moving the movable portion 11 of the fluid dispensing container 5, such as, for example, a lead screw, a stem, a lever, a roller or rollers, a rack, etc. The metering drive system 46 is provided to effect the controlled movement of the metering drive 14, and hence the plunger 11, into the fluid dispensing container 5 to accurately dispense fluid 6 contained within the fluid dispensing container 5.

FIG. 1 shows one embodiment of metering drive 14 and plunger 11. As shown in FIG. 1, the metering drive 14 may include a substantially flat tip (i.e., distal end) that may selectively engage/disengage the plunger 11. The metering drive 14 shown in FIG. 1 is disengaged from the plunger 11.

FIGS. 2A and 2B show another exemplary metering drive 14 and plunger 11, and the interface between the metering drive 14 and plunger 11. As shown in FIGS. 2A and 2B, the plunger 11 may include a round (concave) portion or recess 11a that receives a corresponding round (convex) portion or tip 14a of the metering drive 14. FIG. 2A shows the metering drive 14 disengaged (i.e., backed off) from the plunger 11 and FIG. 2B shows the metering drive 14 engaged (i.e., in contact) with the plunger 11.

A seal 15 may be provided between the plunger 11 and sidewall 12 of the fluid dispensing container 5. The seal 15 substantially prevents fluid 6 contained within the vial 5 from passing between the plunger 11 and a sidewall 12 of the fluid dispensing container 5. An interference fit of the plunger 11 within the fluid dispensing container 5 may provide the necessary seal. Alternatively, a separate seal, such as a gasket or o-ring type seal, may be provided. As shown, for example in FIGS. 1 and 2A, multiple seal points 15a, 15b can be provided between the fluid dispensing container 5 and the plunger 11. Preferably, the seal 15 hermetically seals the interface between the plunger 11 and the interior of the fluid dispensing container 5.

In the illustrated embodiments of FIGS. 1, 2A and 2B, the metering drive 14 comprises a lead screw that can selectively make contact with a back of the plunger 11 to cause the plunger 11 to slide forward in to the fluid dispensing container 5. For example, when the smart metering drive system 46 is activated the metering drive 14 moves forward and seeks the plunger 11. When the metering drive 14 contacts the plunger 11 it begins to engage the plunger 11. Once the metering drive 14 and plunger 11 are engaged, the metering drive 14 provides an actuation sliding force to push the plunger 11 forward in to the fluid dispensing container 5. When engagement of the metering drive 14 and the plunger 11 is sensed, the smart metering drive system 46 commences the measuring of the volume or dose to be delivered. The controlled forward motion of the plunger 11 by the smart metering drive system 46 reduces the volume available within the fluid dispensing container 5 for holding a fluid 6 (i.e., the net fluid volume) thus causing a specific volume of fluid 6 contained within the fluid dispensing container 5 to be dispensed through the outlet opening 7. The smart metering drive system drive 46 may be controlled by appropriate electronics and software.

In the illustrated exemplary embodiment wherein the metering system 1 is incorporated in a pulmonary drug delivery device 70, a nozzle 16 may be provided in fluid communication with the outlet opening 7 of the fluid dispensing container 5 (see, for example, FIGS. 1, 2A, 2B, 3 and 10). A flow passageway 17 may be provided to fluidly connect the outlet opening 7 of the fluid dispensing container 5 to the nozzle 16. The nozzle 16 facilitates delivery of the fluid 6 in the proper form depending on the particular application that the metering system 1 is serving. For example, for a pulmonary drug delivery device 70 (see FIG. 10), the nozzle 16 can be designed to produce an aerosol egress that may be inhaled by the user. As shown, the nozzle 16 may include a plurality of annularly arranged spray sites 18 for aerosol egress. Additional details of suitable nozzles that may be used with the metering system for accounting for differential thermal expansion of the present invention are disclosed in related and commonly assigned application: U.S. Provisional Patent Application No. 60/773,239, VNTA-0004 filed on Feb. 14, 2006 and entitled "DISSOCIATED DISCHARGE EHD SPRAYER WITH ELECTRIC FIELD SHIELD"; the entirety of said application is hereby incorporated by reference herein.

FIG. 3 shows a detail view of an exemplary metering system 1 in the area of a nozzle 16. As shown, the accurate metering system 1 also allows any nozzle dead volume 16a to be at least partially filled prior to dosing thereby helping to ensure more accurate metering. This priming feature helps improve dose content uniformity and reduce dose variability, especially between first and second actuations. The plunger seeking event and engagement of the plunger by the metering drive reduces actuation volume variability between successive dose actuations by at least partially filling nozzle and/or valve dead volume 16*a*. The dead volume may be filled with fluid as the metering drive engages the plunger up until the cracking pressure of the valve or nozzle is sensed. Once cracking is sensed, then a desired amount of fluid may be metered. Priming the metering system prior to fluid delivery helps ensure more accurate metering. This feature also allows single and dual (multiple) doses to be prescribed with the same device.

As shown in FIG. 1, a valve 20 may be disposed between the outlet opening 7 of the fluid dispensing container 5 and the nozzle 16. The valve 20 is preferably a one-way device that helps control the dispensing of the fluid 6 from the fluid dispensing container 5. The valve 20 includes sufficient cracking pressure to prevent formulation weeping during volumetric thermal expansion. One suitable valve device includes a plug-type valve. Preferably, the valve 20 is designed and constructed to allow for multiple and repeated dispensing cycles. In an exemplary plug type one-way valve 20, for example, a plug (not shown) is provided with a resetting mechanism (not shown) that resets the plug to a closed position at the end of a delivery cycle. The resetting mechanism may include any conventional means, such as gravity, a tether, the deformation of a part of the valve, etc.

The valve 20 may also be designed to prevent foreign objects, such as dirt, dust, air, microbes, and the like from entering the fluid dispensing container. For example, the valve may also include an elastomeric sheath type valve, a flapper valve, a slit valve, a duck bill valve, and the like to prevent foreign objects from entering the fluid dispensing container. The valve 20 may include a passive type valve, as described above, or an active type valve. In an embodiment having an active valve, the valve 20 may be opened, for example, upon sensing of the engagement of the metering drive 14 and the plunger 11, to fill any dead volume thus priming the accurate metering system 1.

As shown in FIG. 1, differential thermal expansion/contraction between the fluid dispensing container 5 and the fluid 6 contained within the fluid dispensing container 5 may cause the plunger 11 to slide relative to the fluid dispensing container 5. A decrease in temperature typically causes fluid contraction, which can cause the plunger 11 to pull away from the metering drive 14 (as represented by arrow 22 of FIG. 1). This contracting fluid volume may cause the plunger 11 to be pulled in. If the plunger 11 is not free to move in response to this contracting fluid volume, the pulling the plunger 11 inward may create a low enough fluid dispensing container pressure to cause out-gassing of air or a vapor phase of the liquid in the fluid dispensing container 5. Either of these latter conditions may cause bubbles in the fluid dispensing container 5 and create compliance which adversely impacts metering accuracy. The present invention solves this problem by providing a plunger 11 that is free to move in response to contracting fluid volume. As the fluid volume in the fluid dispensing container 5 contracts, the plunger 11 is pulled inward with the contracting fluid volume thereby mitigating the effects of differential thermal contraction between the substantially rigid fluid dispensing container and the fluid 6 contained within the fluid dispensing container 5.

In contrast, an increase in temperature typically causes net fluid expansion, which can force the plunger 11 toward the metering drive 14 (as represented by arrow 23 of FIG. 1). If the plunger is not free to move in response to this fluid expansion, then the expanding fluid volume may cause fluid 6 to be expressed (discharged) from the fluid dispensing container 5. The present invention solves this problem by providing a plunger 11 that is free to move in response to expanding fluid volume. As the fluid volume in the fluid dispensing container 5 expands, the plunger 11 is pushed rearward with the expanding fluid volume thereby mitigating the effects of differential thermal expansion between the substantially rigid fluid dispensing container and the fluid 6 contained within the fluid dispensing container 5.

By way of example, if the fluid 6 contained within the fluid dispensing container 5 includes ethanol, ethanol expands at a rate that exceeds the expansion rate of a fluid dispensing container made from rigid polymer over an intended device storage range of about 0 to 45 degrees C. In an exemplary ethanol-based fluid dispensing container, the differential volume could increase or decrease by approximately 5% from a 45 degree C. temperature change.

In order to reduce and/or prevent leakage with increasing temperature, or out-gas, vaporization with decreasing temperature associated with a typical constant volume metering system, the present invention mitigates the adverse effect of differential thermal expansion/contraction by providing a substantially constant pressure and allowing the volume to change as the fluid expands and/or contracts with changing temperature. In order to provide for a changing volume, the fluid dispensing container 5 includes a movable portion 11 that moves as the fluid 6 within the fluid dispensing container 5 expands and/or contracts. In the illustrated embodiments, the movable portion of the fluid dispensing container includes a piston-type plunger 11.

In order for the piston plunger 11 to slide backwards in response to an expanding fluid within the fluid dispensing container, the metering drive system 46 moves the metering drive 14 away from the piston plunger 11, thus allowing the plunger 11 to move backwards over the high temperature range. In the illustrated embodiments, the metering drive system includes a metering drive 14 that can be backed off of the piston plunger 11 (see FIG. 2A).

FIGS. 2A and 2B show another exemplary metering system 1 that mitigates differential thermal expansion/contraction. As shown in FIG. 2A, the metering drive 14 is backed away from the plunger 11. In this disengaged position, a clearance 25 exists between the metering drive 14 and the plunger 11. The clearance 25 allows the plunger 11 to slide backward during thermal expansion of the fluid 6 without contacting the metering drive 14. Preferably, the clearance 25 is sized to account for all possible expansion distances based on the fluid contained within the fluid dispensing container, the materials of the components of the metering system, the anticipated operating environment of the dispensing device, and the like.

FIG. 2B shows the metering drive 14 in the engaged position. In the engaged position, the metering drive 14 is in contact with the plunger 11. Preferably, the distal end of the metering drive 14 includes a shape that corresponds to a mating surface 11 on the back end of the plunger 11. As shown in FIGS. 2A and 2B, the distal end of the metering drive 14 includes a rounded mating surface 14A and the back end of the plunger 11 includes a recessed mating surface 11*a*.

In one embodiment, the mating surfaces 11*a*, 14*a* between the plunger 11 and the metering drive 14 may be designed to further facilitate the sensing of the engagement between these two components. For example, the mating surfaces 11*a*, 14*a* may comprise surfaces (e.g., rough surfaces) that increase the friction between the two mating surfaces during the engagement process. The mating surfaces may result in increased friction between the two surfaces and an increase in current/ torque on the motor/metering drive because of the increased power required to turn the metering drive.

A sensing mechanism 30 is provided to determine when the metering drive 14 becomes engaged with the plunger 11. Engagement of the metering drive 14 with the plunger 11 may be used by the metering drive system as a starting point for the incremental movement of the metering drive 14 for delivering an accurate and/or a precise dose measured as a set volume. Preferably, the accurate metering system 1 can also account for one or more of fluid expansion/contraction, dead volume, compliance in valve 20 and/or nozzle 16, and the like. As such, the starting point may be any point from contact, through resistance or compliance take-up (i.e., priming), to fluid delivery.

Figure 4:
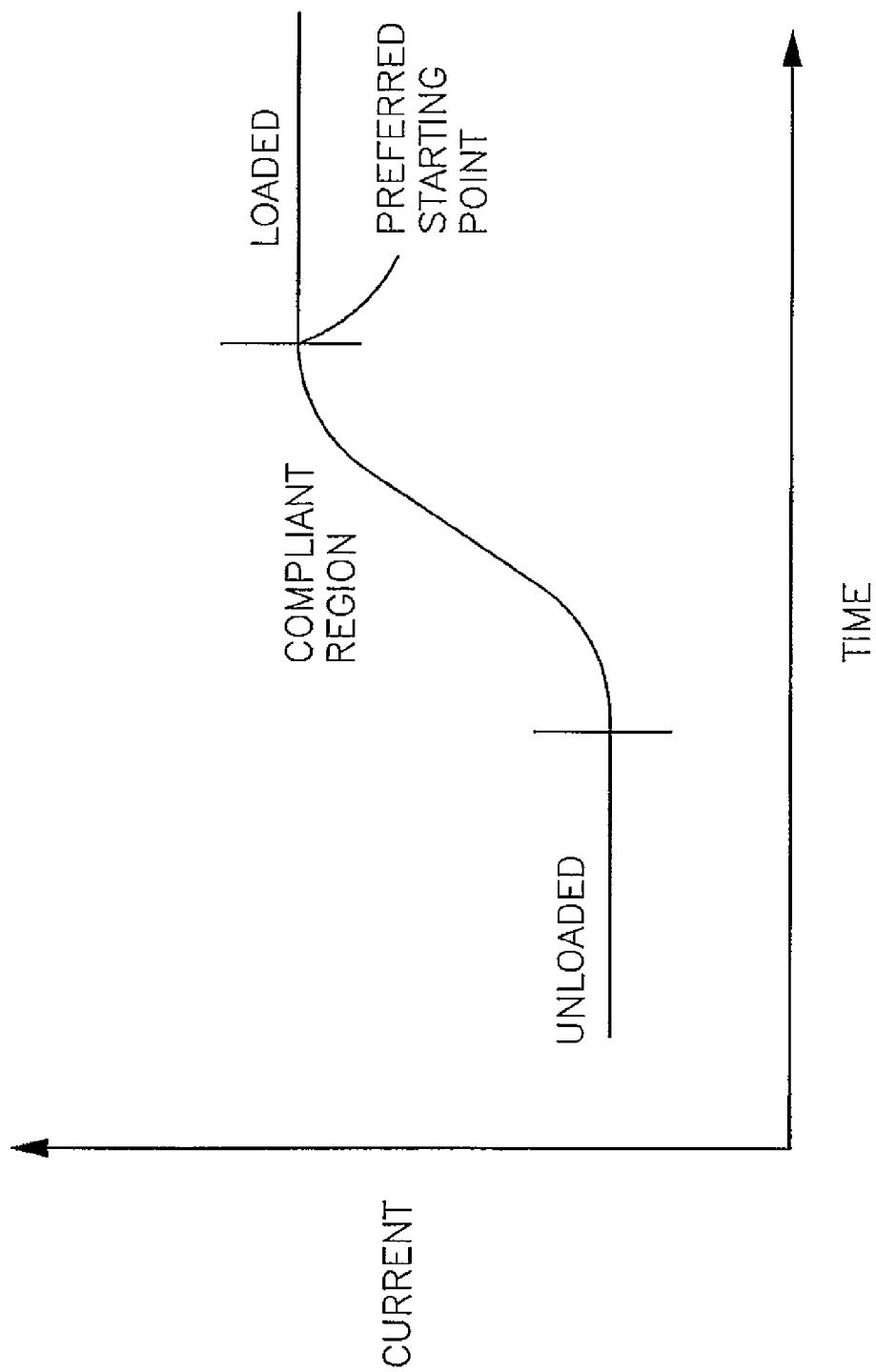
FIG. 4 is a graph showing an exemplary current curve for sensing an unloaded and loaded motor condition.

The sensing mechanism 30 can include, for example, an electrical circuit that senses the load on the metering system drive motor 31 and determines when the metering drive 14 is unloaded and loaded. The current draw from the motor 31 may be monitored to determine when the current ramps up from the unloaded to loaded condition, see for example, FIG. 4. The starting point can be determined based on the rate of change of the load (differential) on the motor 31. In an embodiment, the starting point is the point where the current curve flattens out at the top (i.e., when the motor is loaded), as shown in FIG. 4. The sensing mechanism can include other types of sensors, such as for example, a switch type sensor that senses a completed electrical circuit when the metering drive contacts the plunger, an optical sensor that senses the illumination and/or blocking of a light source when the metering drive contacts the plunger, an audio sensor that senses an audio signal of, for example, the motor (i.e., the motor changes pitch with changing torque), and the like. In yet another embodiment, the sensing mechanism can include a torque sensing mechanism.

The smart metering drive system 46 that senses the location of the plunger prior to delivery of the fluid from the fluid dispensing container improves the performance of the metering system and also provides other advantages as well. For example, sensing the location of the plunger with the metering drive provides a solution to metering drive placement at final assembly during manufacturing of the delivery device. Previously, the metering drive had to be very accurately placed or the user had to prime the metering system prior to use. The present invention solves this problem by not requiring any specific metering drive placement at final assembly because the smart metering drive system is capable of locating the position of the plunger prior to fluid delivery.

In another embodiment, the starting point may be the point where delivery of the fluid commences and the point from which the delivery is counted (measured). A counting mechanism 40 may be used to measure the delivery of a precise dose. In the illustrated embodiment, a rotating encoder disk 50 (shown in FIGS. 5 and 7 and described in more detail below) is used to count the travel of the metering drive 14 and hence the volume of fluid 6 dispensed.

Figure 11:
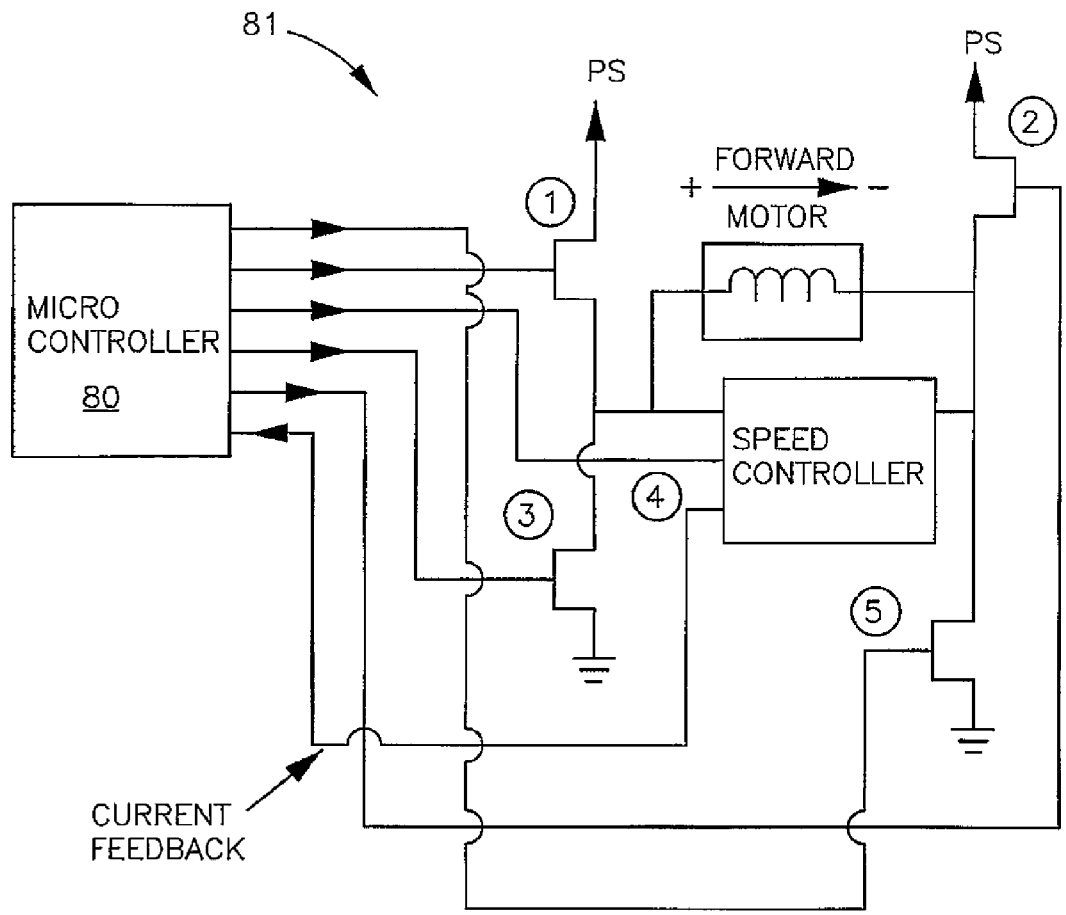
FIG. 11 is an electric schematic diagram of exemplary metering and sensing circuitry that may be used with the accurate metering system.
Figure 12:
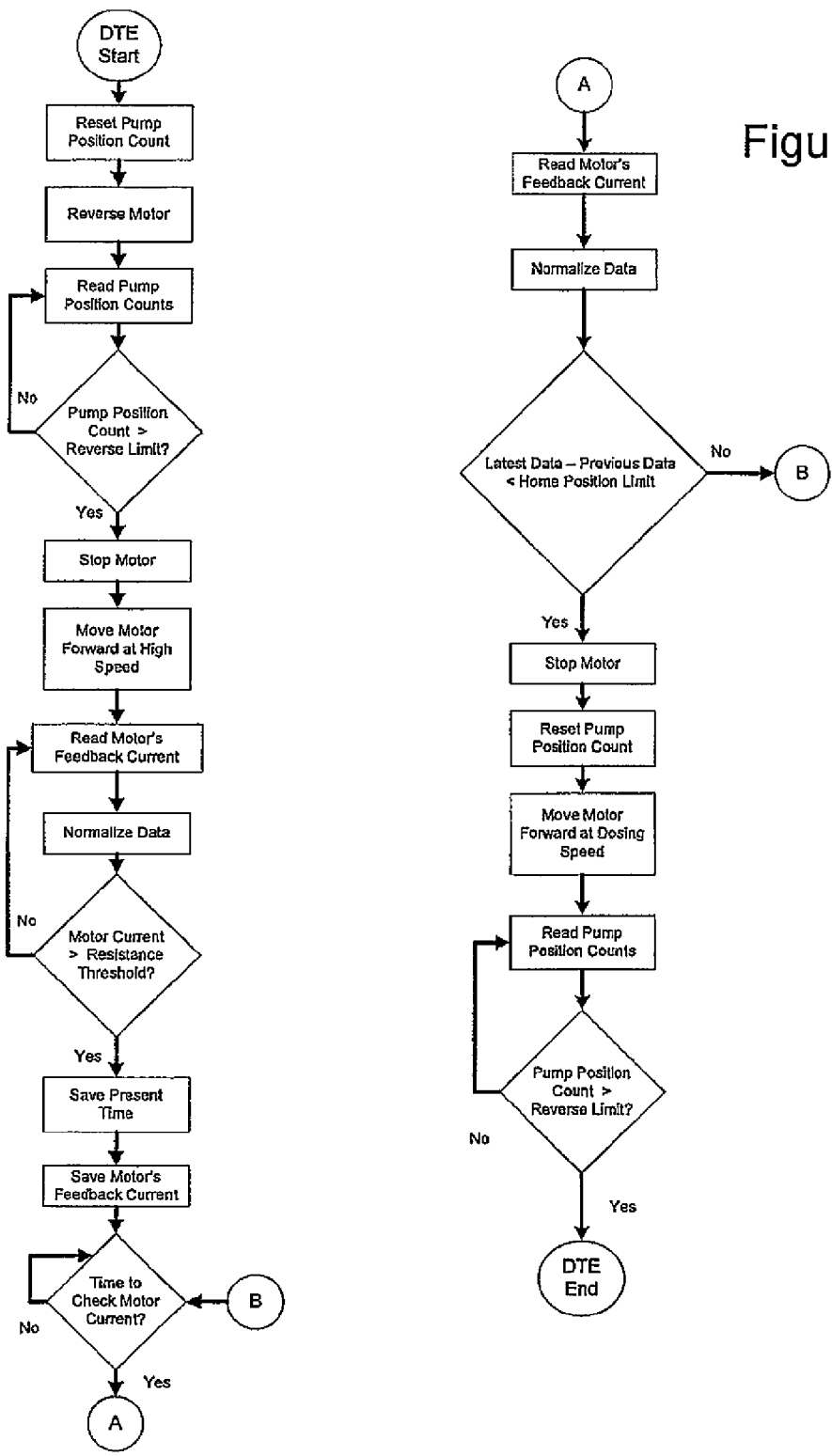
FIG. 12 shows an exemplary flowchart illustrating how the accurate metering system can be used to determine the meter drive position in relation to the fluid.
Figure 13B:
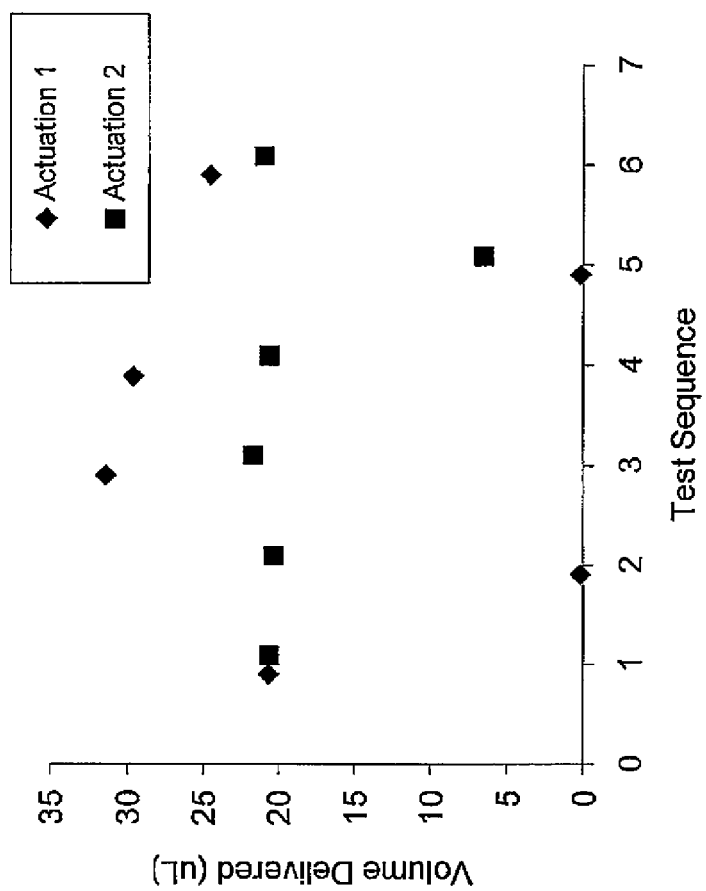
FIG. 13B is a graph showing poor performance of volume delivery without a smart metering drive system and metering drive during the temperature cycling profile.
Figure 13A:
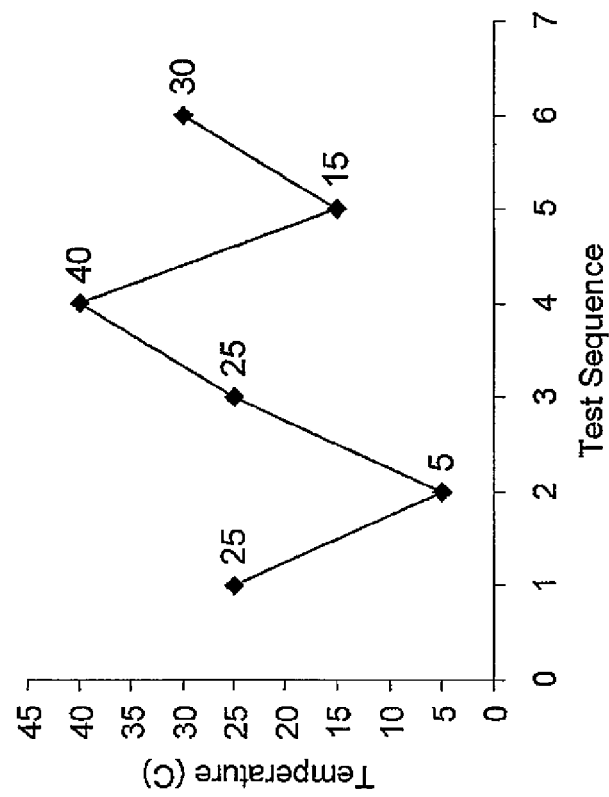
FIG. 13A is a graph showing an exemplary temperature cycling profile.
Figure 14B:
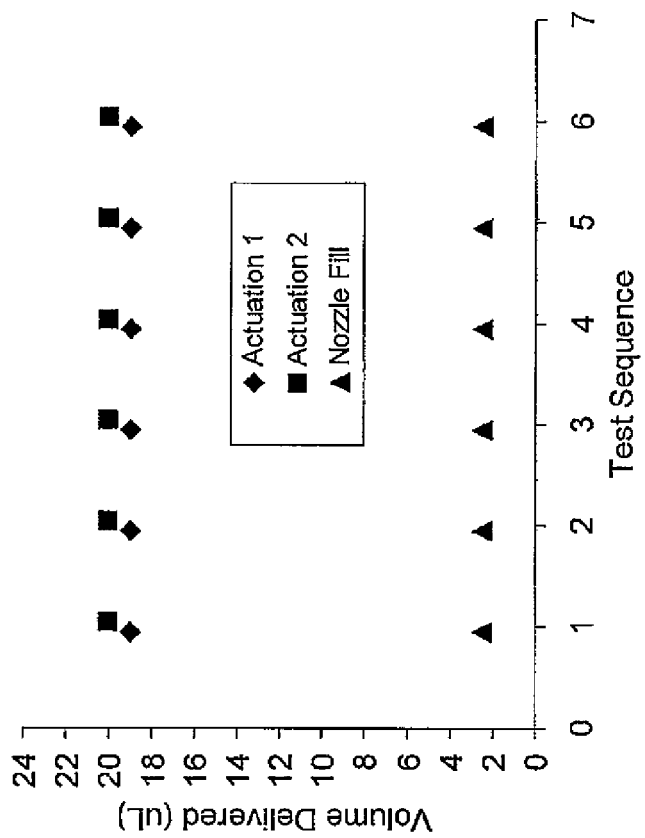
FIG. 14B is a graph showing good performance of volume delivery with a smart metering drive system and metering drive during the temperature cycling profile.
Figure 14A:
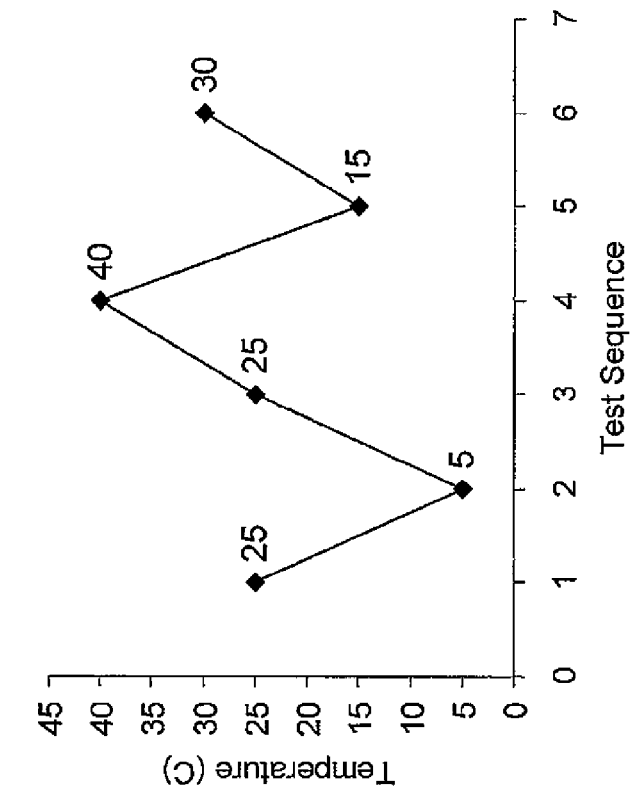
FIG. 14A is a graph showing an exemplary temperature cycling profile similar to that of FIG. 13A.
Figure 15:
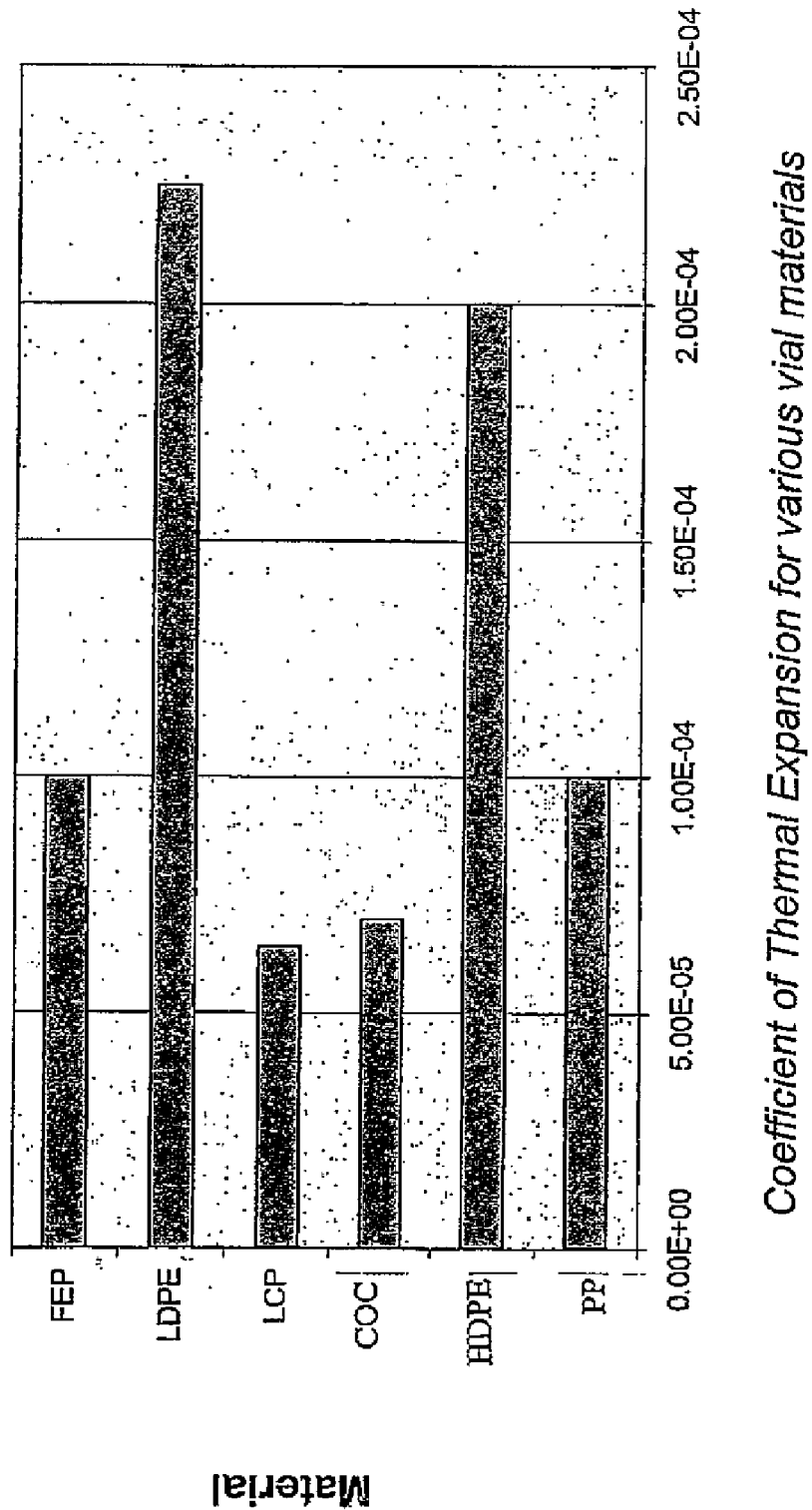
FIG. 15 is a graph showing the coefficient of thermal expansion for several exemplary fluid dispensing container materials.

Exemplary metering and sensing circuitry and logic flow diagrams are shown in FIGS. 11 and 12. In one embodiment, the metering system 1 can use several different methods to sense/determine the position of the pump with respect to the location of the fluid. One exemplary method uses an optical sensor to measure the distance the pump (metering drive) moves. Another means of sensing may measure the electrical current required to turn the motor. This current value may be proportional to the resistance of the pump, and hence indicative of the metering drive engaging the plunger.

As shown, the metering system and method can include creating a profile of the pump's electrical current as it transitions from no resistance to pushing out fluid. These profiles may then be analyzed to determine how it corresponds to pump positioning. FIG. 4 shows an exemplary profile.

The metering system and method may then use the generated profiles of the metering system to decide where the pump is in relation to the fluid. FIG. 12 shows this method based on analysis of one exemplary metering system design. The logic for the encoder can include, for example, a photo interrupter that produces a digital pulse when the sensor's beam hits a gap or window in the encoder wheel. The microcontroller counts the number of digital pulses until the count reaches the preset count. This count may represent the targeted dose volume.

A suitable controller or microcontroller 80 and associated electronic circuitry 81 can be used for the control and operation of the metering system and support systems, such as the sensing mechanism, the counting mechanism, the motor, the gear train, the metering drive, etc. (See FIG. 11). Suitable software and logic algorithms are also included to ensure efficient, accurate, and reproducible metered delivery of fluids even in view of differential thermal expansion/contraction and/or valve/nozzle dead volume. (See FIG. 12).

Figure 5:
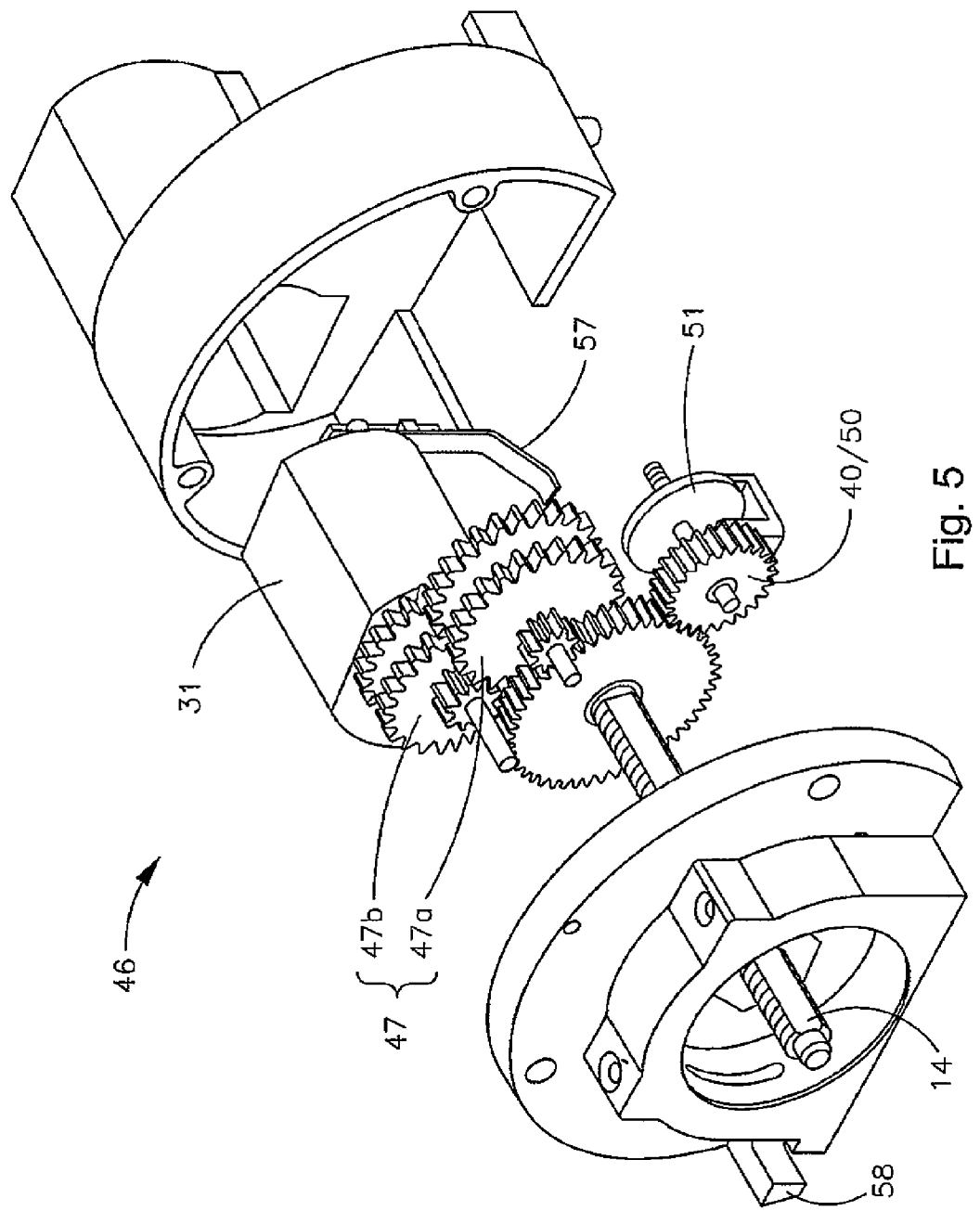
FIG. 5 is a front perspective view of an exemplary meter drive system and metering drive.
Figure 6:
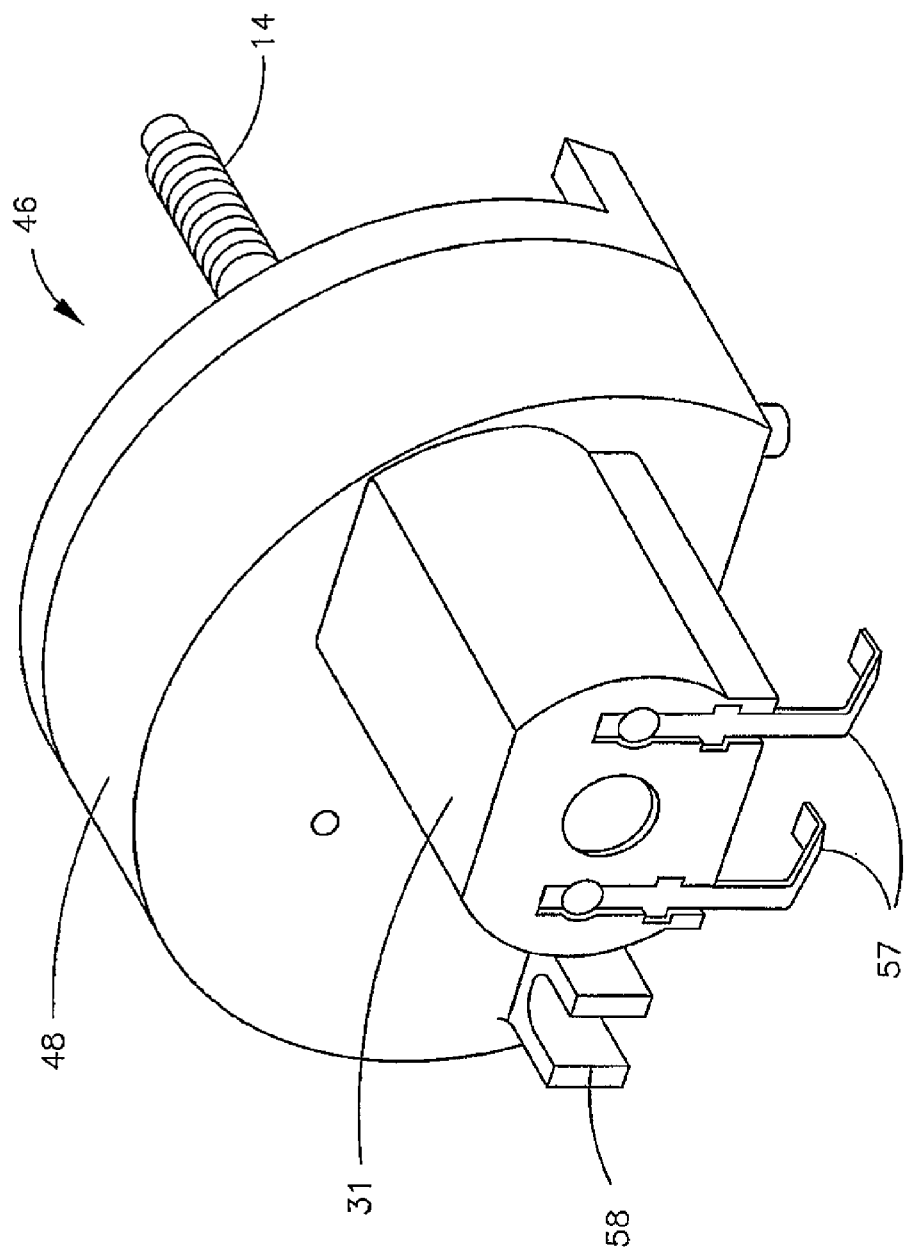
FIG. 6 is a rear perspective view of the exemplary meter drive system and metering drive of FIG. 5.

FIGS. 5 and 6 show an exemplary metering drive system 46 that can be used with the metering system 1 that mitigates differential thermal expansion/contraction. This can be accomplished by providing a means for backing the metering drive off of the plunger when the metering system is not in use, providing a means for allowing the plunger to freely move within the fluid dispensing container in response to fluid volume changed resulting from changes in temperature, and/or providing a means for locating the position of the plunger prior to fluid delivery. Various means/mechanisms can be provided to accomplish each of these features. Several exemplary means/mechanisms are described below.

Figure 10:
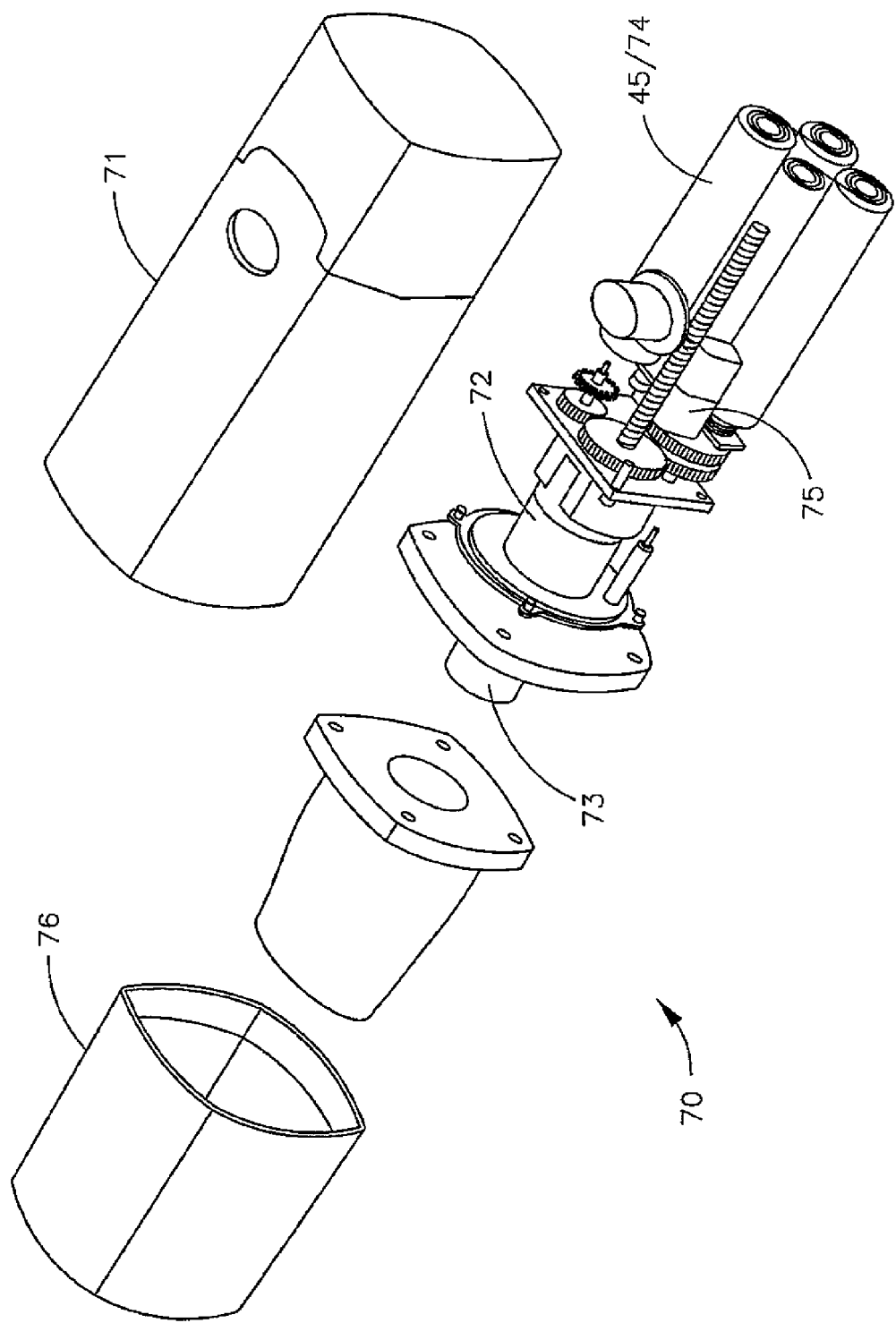
FIG. 10 shows an exemplary dispensing device.

As shown in FIGS. 5 and 6, the power and drive systems can include a motor 31, a drive gear train 47, and a metering drive 14. The power and drive systems may also include a power source 45 (FIG. 10). The power source 45 may include, for example, batteries. The motor 31 may be electrically connected to the power source 45. The motor 31 includes an output shaft that is connected to the metering drive 14 through one or more gears 47a, 47b that comprise the gear train 47. In the illustrated embodiment, the drive gear train 47 couples rotational movement of the motor 31 to axial or linear movement of the metering drive 14. The drive gear train 47 may step up and/or step down the speed of the motor 31 relative to the speed of the metering drive 14.

It is preferred that the metering drive be capable of being backed off the plunger to allow for differential thermal expansion between components in the metering system. In one embodiment, the motor 31 is a reversible motor and allows the metering drive 14 to back off of the plunger 11 so that there is a clearance 25 between the metering drive 14 and the plunger 11 (see FIG. 2A). Alternative means may be provided to back the metering drive off the plunger, such as suitable reversing gears.

In addition, it is preferred that the speed of the metering drive be variable to provide for more time efficient operation of the metering system. In one embodiment, the speed of the metering drive is varied by use of a multiple or variable speed motor 31. For example, the motor 31 may include a two-speed motor that can operate at a first, or relatively high, speed while the metering drive is seeking the plunger 11 and up until the metering drive 14 engages the plunger, and then the motor 31 may operate at a second, and relatively low, speed for controlled delivery of the fluid 6. Thus, a device having a multiple or variable motor can use a high speed to more rapidly engage the plunger.

FIG. 6 shows a rear view of the power and drive systems. As shown in FIG. 6, the gear train 47 is protected by a gear box housing 48. Electrical contacts 57 are provided for electrically connecting the motor 31 to a power source (not shown in FIG. 5 or 6) and providing power to the motor 31. A mounting mechanism 58 may be provided for mounting the power and drive systems to the device housing (not shown).

Figure 7:
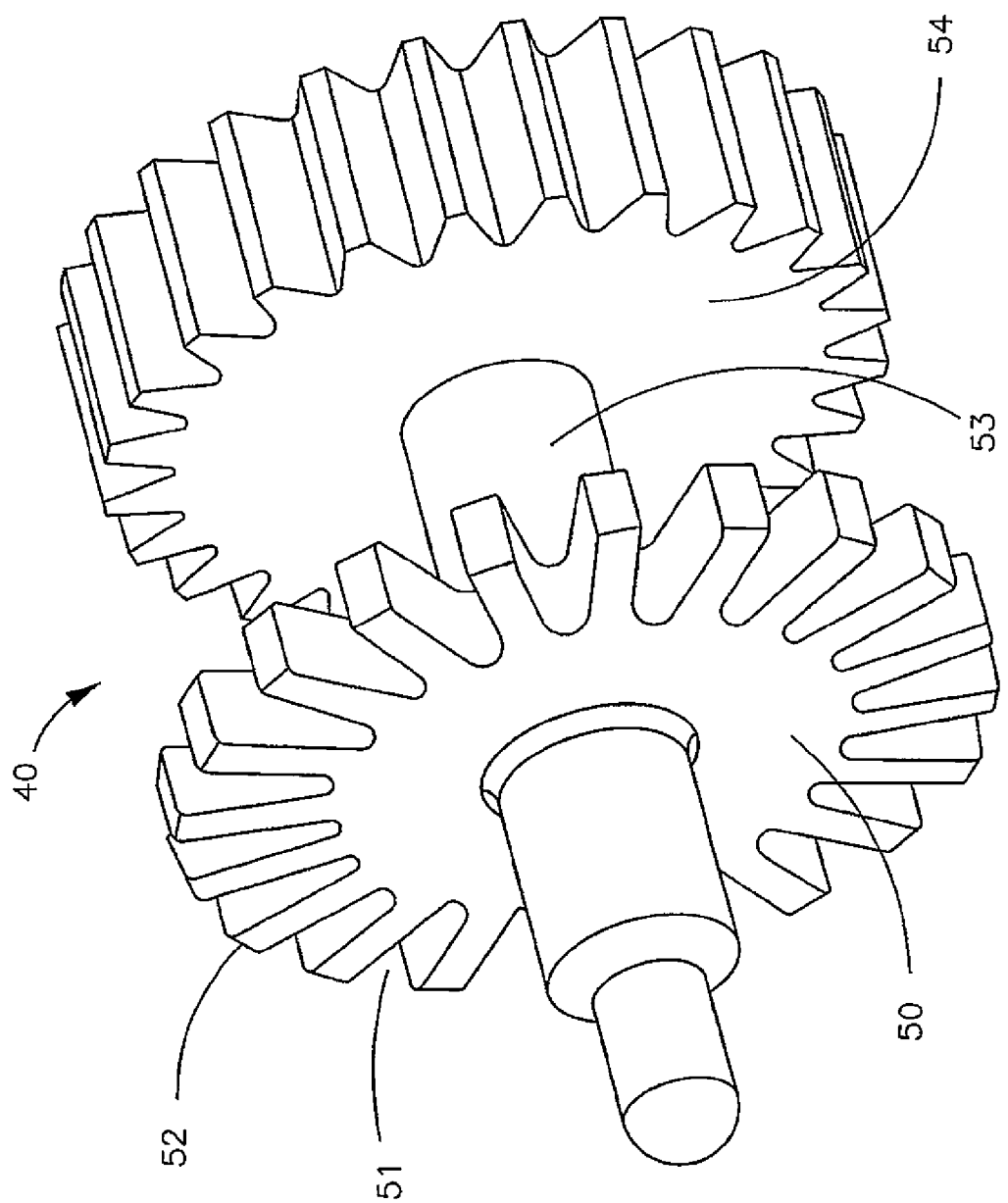
FIG. 7 is a perspective view of an exemplary encoder disk used for dose volume control.

FIGS. 5 and 7 show an exemplary encoder disk 50 that may be used for dose volume control. As shown in FIG. 5, the encoder disk 50 may include a window or windows 51 that can be used to measure the rotation of the encoder disk 50 which correlates to the distance of travel of the metering drive 14. The distance of travel of the metering drive 14 can be used to determine a quantity (i.e., volume) of fluid 6 that is being dispensed.

In a preferred embodiment shown in FIG. 7, the encoder disk 50 includes a plurality of windows 51 (openings, holes, slots, etc.). As shown, the windows 51 are disposed around a periphery 52 of the encoder disk 50. A shaft 53 connects the encoder disk 50 to an encoder disk gear 54. The encoder disk gear 54 is in engagement with the gear train 47 for the metering drive 14 (see FIG. 5). As the metering drive gear train 47 rotates, the encoder disk gear 54 also rotates. A sensor (not shown), such as an optical sensor, can be used to sense the windows 51 as the windows 51 rotate through or pass the sensor. For example, the sensor may include an optical sensor, such as a light diode and a reader.

The advantage of having an encoder disk 50 having a plurality of windows 51 is that more accurate dosing is possible. Generally, the greater the number of windows 51 on the encoder disk 50 or the greater the number of encoder disk rotations per dose volume, the greater the potential accuracy of the metering system. In operation the metering drive 14 is advanced until it contacts the plunger 11. This may be used as the starting point for the metered dispensing of fluid 6 from the fluid dispensing container 5. Once contact of the metering drive 14 to the plunger 11 is sensed, the metering system 1 can measure the dose several ways, such as for example, counting the number of windows 51 that pass by a reference point as the encoder disk 50 rotates. Also, in an extreme accuracy metering system, the encoder disk 50 may be accurate enough so it can be used to account for changes in fluid volume resulting from changing temperature. In this regard, an accurate dose (as opposed to volume) may be delivered. This further allows the accurate metering system 1 to deliver more precise doses and not just a precise volume. In addition, a multi-slotted encoder 50 may allow for changes in dose volume and flow rate via software. This allows the device to be used with other potential fluids/compounds.

One way to control dose volume is to count the number of windows 51 that pass by the sensor as the encoder disk 50 rotates. Another way is to rotate the encoder disk 50 a known amount, such as one full revolution, etc. Since the location of the plunger 11 is not known until the metering drive 14 contacts the plunger 11, an encoder disk 50 having a plurality of windows 51 helps to ensure that one of the windows will be in a sensing zone at start-up. Generally, having a greater number of windows 51 helps ensure that a window is in the sensing zone at plunger engagement resulting in more accurate metering. In the exemplary encoder disk 50 shown in FIG. 7, the encoder disk 50 includes twenty windows, each window representing a known volume of fluid.

Figure 8:
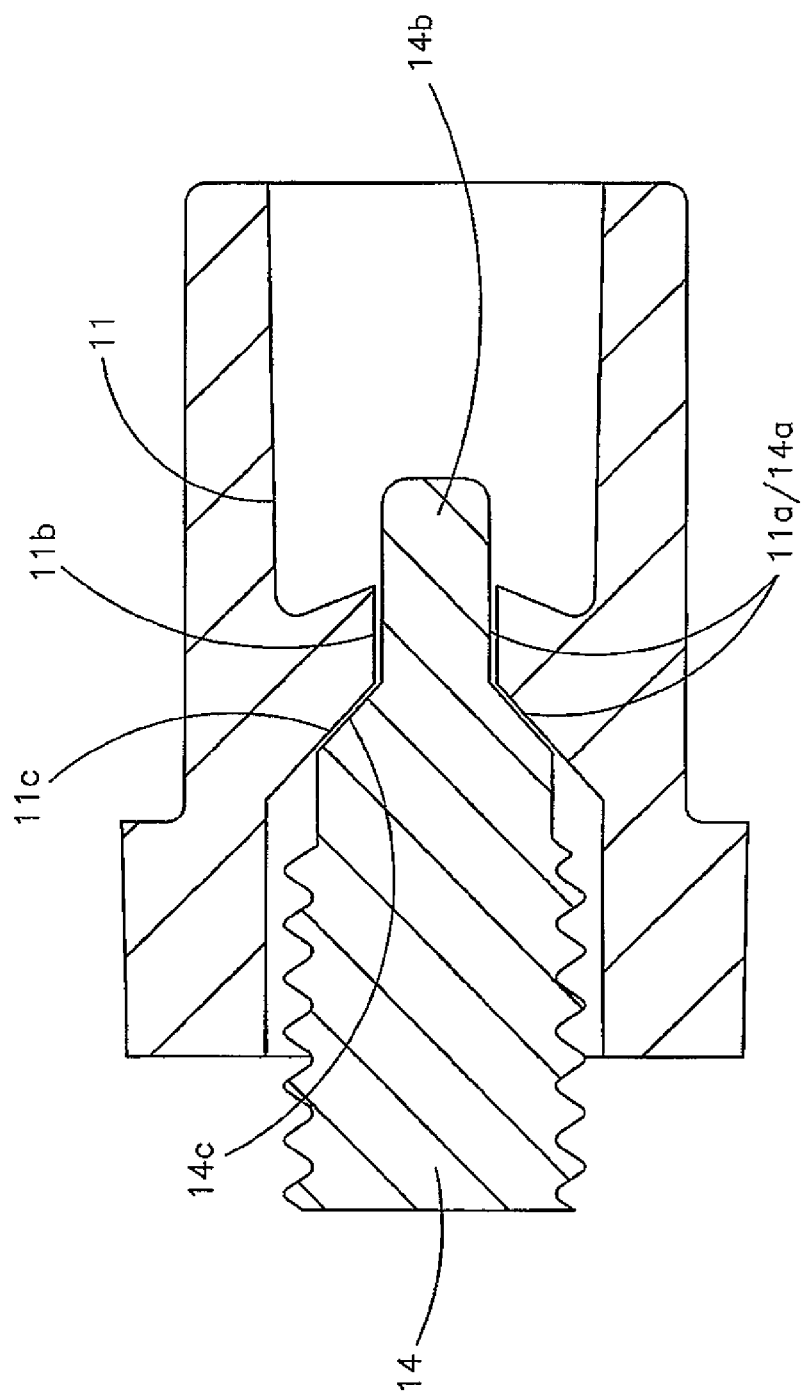
FIG. 8 is a cross sectional detail view showing an exemplary metering drive engaging an exemplary piston.

FIG. 8 shows a detail of the engagement between an exemplary metering drive 14 and an exemplary piston plunger 11. Preferably, the metering drive 14 includes a tip geometry that facilitates the sensing of the metering drive 14 contacting and engaging the plunger 11. Also, as shown in FIG. 8 the mating surface 14a of the metering drive 14 preferably has a shape that corresponds to the mating surface 11a of the plunger 11. As shown, the metering drive 14 includes a cylindrical portion 14b and tapered shoulders 14c (i.e., a conical portion). The contact interface or mating surface of the plunger 11a includes an opening or recess 11b for receiving the cylindrical portion 14b and a tapered surface 11c that contacts the shoulders of the conical portion 14c of the metering drive 14. Preferably, the shape and design of the mating surfaces 11a, 14a between the metering drive 14 and the plunger 11 also provides a piloting function to ensure good contact and form a friction contact therebetween. This design and construction of the mating surfaces may also help to amplify the change in the motor current for more optimal sensing of the plunger.

The accurate metering system 1 preferably includes a design and construction that allows the movable portion 11 to move (e.g., slide) with respect to the fixed portion of the fluid dispensing container 5 while at the same time sealing the fluid 6 within the reducible volume defined by the fixed and movable portions of the fluid dispensing container. In this regard, the fluid dispensing container and plunger design may include a sliding force that allows that plunger to move freely with respect to the fluid dispensing container in response to differential thermal expansion/contraction, while at the same time having sufficient sealing force to preserve the integrity of liquid formulation within the fluid dispensing container. In an embodiment, the design of the fluid dispensing container and the plunger includes consideration of, for example, diametral interference between the fluid dispensing container and the plunger as a function of temperature and also accounts for various potential materials for the components. The fluid dispensing container and plunger design, as well as the sliding force (e.g., actuation sliding force, expansion sliding force, and contraction sliding force) and sealing force, may depend in part on the fluid contained within the fluid dispensing container.

In order for the dispensing device to work properly, the sliding limit should allow the plunger 11 to slide back and forth within the fluid dispensing container 5 in response to differential thermal expansion/contract caused by temperature changes. The required sliding limit is the force/pressure required to ensure that the plunger moves before the cracking pressure of the valve is reached during differential thermal expansion and the force/pressure required to ensure that the plunger moves with ambient atmospheric pressure during differential thermal contraction.

For example, in the illustrated syringed based metering system, a differential thermal expansion sliding force is the force required to cause the plunger to slide rearward in response to differential thermal expansion resulting from an increase in temperature. Preferably, the differential thermal expansion sliding force is less than a cracking pressure of the outlet valve. A differential thermal contraction sliding force is the force required to cause the plunger to slide forward in response to differential thermal contraction resulting from a decrease in temperature. Preferably, the differential thermal contraction sliding force is less than the force exerted by available atmospheric pressure. Preferably, the sealing force multiplied by a coefficient of friction for a given material pair is less than a differential thermal expansion and/or contraction sliding force.

Likewise, in order to work properly the dispensing device preferably includes sufficient sealing force between the fluid dispensing container and the plunger to prevent the ingress of contaminants into the fluid dispensing container 5 and/or the egress of fluid out of the fluid dispensing container 5 between the fluid dispensing container 5 and the plunger 11. The required sealing limit is the force/pressure required to provide a sufficient seal between the fluid dispensing container and the plunger to preserve integrity of liquid formulation within the interior volume of the fluid dispensing container.

Figure 9:
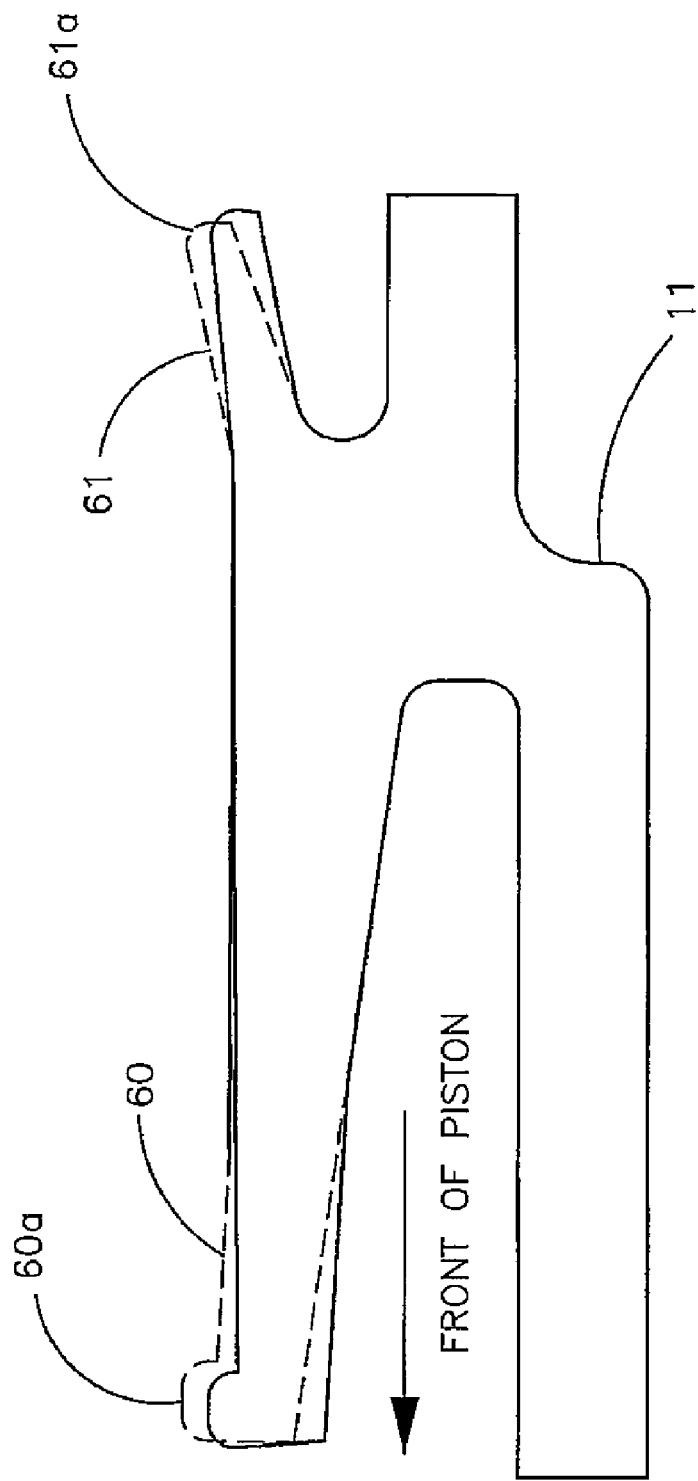
FIG. 9 is a detail showing a portion of an exemplary piston plunger that can be used with a syringe-based metering system.

FIG. 9 is a detail showing a front portion of an exemplary piston plunger 11 that can be used with a syringe-based metering system 1. FIG. 9 represents an exemplary piston plunger 11 that in operation may be disposed inside a fluid dispensing container 5. As shown in FIG. 9, in one embodiment the piston plunger 11 can include a forward arm 60 and a rearward arm 61 that are bias toward the fluid dispensing container sidewall (not shown in FIG. 9). For a syringe-based metering system 1 having a cylindrical syringe and plunger, the arms 60, 61 are biased radially outward. As can be seen, the distal ends 60a, 61a of the forward and rearward arms 60, 61 experience the most interference with the fluid dispensing container sidewall and help seal the fluid within the interior of the fluid dispensing container 5.

The interference between the plunger 11 and the fluid dispensing container 5 can be optimized for peak performance via material stress relaxation. Material stress relaxation (creep) decreases the sensitivity of the design to manufacturing tolerances. Also, material stress relaxation allows the components to be molded on the high side (i.e., more interference) because the materials are allowed to relax to steady state at initial assembly.

FIG. 10 shows an exemplary device 70 for developing pharmaceutical products for inhalation by utilizing electrohydrodynamic (EHD) aerosolization technology. Pulmonary devices that are based on electrohydrodynamic (EHD) aerosol delivery enable efficient, safe and consistent delivery of drugs to and through the lungs.

As shown in FIG. 10, the exemplary inhaler device 70 includes a containment unit 71, a dose metering system 72, aerosol generation nozzle 73, a power supply 74, a microprocessor 75, and a cover 76, which together offer multi-dose or unit dose device options. The illustrated inhalation devices 70 utilizing Mystic™ technology (EHD), deliver a low velocity, soft (isokinetic) cloud of uniformly sized particles with over about 80 percent of the drug getting to the lungs. This is accomplished without the need for liquid propellants or other pressurized systems.

The therapeutic mist generated by the Mystic™ technology dispersion can deliver either liquid solutions or suspensions, including, for example, aqueous liquids, non-aqueous liquids, and suspensions of synthetic and biological compounds. In the spray nozzle 73 of a typical EHD delivery device, fluid flows over an electric field (generated with, for example, small batteries), where an electric charge builds up on the fluid surface. When the fluid exits the nozzle, the repelling force of the surface charge overcomes the surface tension of the fluid, forming a soft mist droplet aerosol. The particle size distribution of the aerosol can be controlled by adjusting a number of variables, such as physical and chemical properties of drug formulations, formulation flow rate, operating conditions, the electric field, and the like.

In an alternative embodiment (not shown), the metering system may include a pouch defining a volume for containing a fluid. Preferably, the pouch is volumetrically reducible. The pouch includes an outlet opening for allowing the fluid contained within the pouch to be expelled from the pouch. The pouch also includes a mechanism for allowing the volume of the pouch to be reduced. For example, one or more rollers may be provided for engaging the pouch such that the volume of the pouch can be reduced as the one or more rollers turn and squeeze the pouch, thus causing the fluid contained within the pouch to be expelled through the outlet opening. The pouch may move relative to the one or more rollers, the rollers may move relative to the pouch, and/or the pouch and roller may more relative to one another.

In accordance with the present invention, the one or more rollers comprising the metering system drive in this embodiment would be capable of being backed off of the pouch when the metering system is not in use. This would allow mitigation the and differential thermal expansion between the pouch and the fluid contained within the pouch.

EXAMPLES

The performance of one embodiment of the accurate metering system 1 was evaluated using an ethanol fluid. FIG. 13A is a graph showing an exemplary temperature cycling profile. A series of test sequences were run, with each test sequence having a different temperature. For example, test sequence no. 1 included a temperature of 25 degrees C.; test sequence no. 2 included a temperature of 5 degrees C.; test sequence no. 3 included a temperature of 25 degrees C.; test sequence no. 4 included a temperature of 40 degrees C.; test sequence no. 5 included a temperature of 15 degrees C.; test sequence no. 6 included a temperature of 30 degrees C. As the temperature fluctuates, differential thermal expansion/contraction occurs between the fluid and the dispensing device.

FIG. 13B is a graph showing the performance of volume delivery of a metering system that does not account for differential thermal expansion/contraction (i.e., a metering system without a smart metering drive system and metering drive) during the temperature cycling profile corresponding to FIG. 13A. As can be seen in FIG. 13B, the metering system delivered inconsistent volumes during the test sequences. This poor performance is caused by the metering system not accounting for differential thermal expansion/contraction. For example, because the plunger may move during temperature changes in a syringe-based metering system, the location of the plunger may be unknown in relation to the metering system drive and hence accurate metering may not be possible. The metering system was allowed to equilibrate at temperature prior to sampling.

FIG. 14A is a graph showing an exemplary temperature cycling profile similar to that of FIG. 13A. FIG. 14B is a graph showing good performance of volume delivery in a metering system that accounts for differential thermal expansion/contraction (i.e., a metering system with a smart metering drive system and metering drive) during the temperature cycling profile. As can be seen in FIG. 14B, the actuation of the metering system and the volume delivered is consistent during each of the test sequences. The reason for this good performance is that the metering system has accounted for differential thermal expansion/contraction. For example, in a syringe-based metering system 1 having a smart metering drive system 46, the piston plunger 11 is first located by the smart metering drive system 46 and a starting point for fluid delivery is set. The proposed dose can then be administered. The metering system 1 having a smart metering drive system 46 and a metering drive 14 to account for differential thermal expansion/contraction provides more efficient, accurate, and reproducible metering.

FIG. 15 is a graph showing the coefficient of thermal expansion for several exemplary rigid fluid dispensing container materials. Preferably, the material for the fluid dispensing container 5 is determined based, in part, on the material of the piston plunger 11, the fluid 6 contained within the fluid dispensing container 5, and the other components of the metering system 1. For example, preferably the fluid dispensing container material has a favorable thermal expansion rate, a better tribological behavior with the piston plunger material, low chemical compatibility issues with valve elastomers, and the like.

Figure 16A:
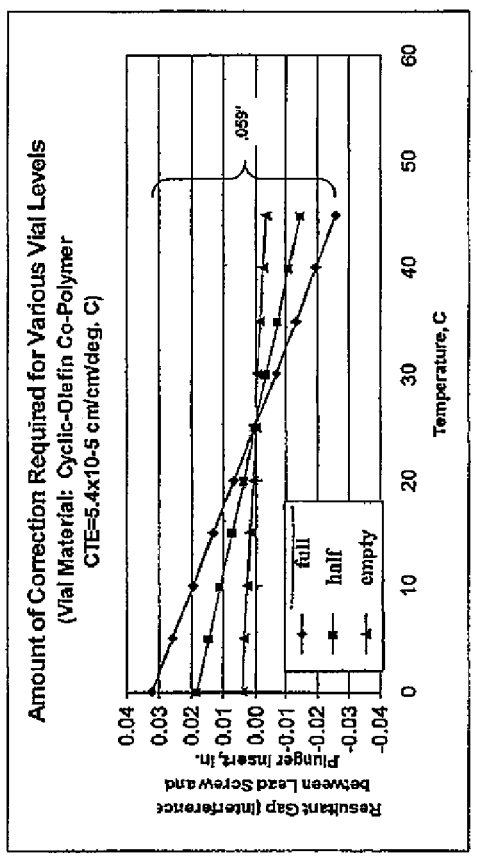
FIGS. 16A and 16B are graphs comparing the resultant gap between the metering drive and the plunger insert as a function of temperature for two different exemplary fluid dispensing container materials.
Figure 16B:
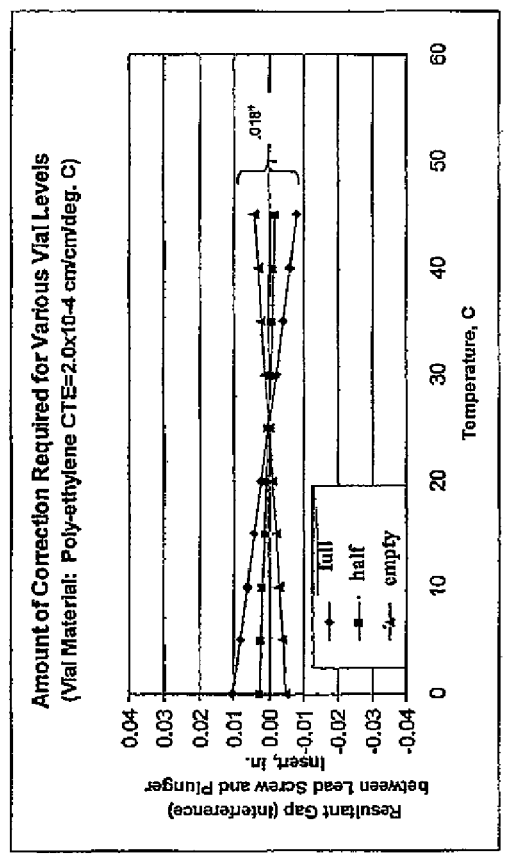

FIGS. 16A and 16B are graphs comparing the resultant gap between the metering drive system (i.e., the metering drive 14) and the movable portion of the fluid dispensing container (i.e., the plunger insert 11) as a function of temperature for two different exemplary fluid dispensing container materials and for fluid dispensing containers having different fluid dispensing container volume content. As shown in both figures, the resultant gap or clearance 25 between the metering drive 14 and the plunger 11 generally decreases with increasing temperature (e.g., as the plunger slides rearward). Note that with extremely low volume remaining in the fluid dispensing container, this generalization may not hold true—since the fluid dispensing container is a relative large structure compared to the volume of fluid in the fluid dispensing container when the fluid dispensing container is almost empty—and the fluid dispensing container may actually expand more than the low volume of fluid (see e.g., FIG. 17B for 0 doses). In addition, the resultant gap 25 also increases as the volume of fluid 6 in the fluid dispensing container 5 increases. Increased fluid volume in the fluid dispensing container is represented by the increased number of doses. For example, at any given temperature the resultant gap 25 is greater for the fluid dispensing container containing 120 doses than the resultant gap for a fluid dispensing container having 60 doses.

FIGS. 16A and 16B also show a comparison of two fluid dispensing containers made from materials having different coefficients of thermal expansion (CTE). The fluid dispensing container of FIG. 16A is made from Cyclic-Olefin co-polymer and has a CTE=$5.4 \times 10^{-5}$ cm/cm/degree C. The fluid dispensing container of FIG. 12B is made from polyethylene and has a CTE=$2.0 \times 10^{-4}$ cm/cm/degree C. As can be seen, the fluid dispensing container material has an effect on the resultant gap or clearance 25 between the metering drive 14 and the plunger 11. In FIG. 16A, the resultant gap 25 for the fluid dispensing container made from Cyclic-Olefin co-polymer fluctuates by about 0.059 inches over a temperature variant of about 0-45 degrees C. In FIG. 16B, the resultant gap 25 for the fluid dispensing container made from polyethylene fluctuates by about 0.018 inches over a temperature variant of about 0-45 degrees C.

While systems and methods have been described and illustrated with reference to specific embodiments, those skilled in the art will recognize that modification and variations may be made without departing from the principles described above and set forth in the following claims. Accordingly, reference should be made to the following claims as describing the scope of disclosed embodiments.

What is claimed:

1. An accurate metering device comprising:
   (a.) a fluid dispensing container for containing a fluid to be dispensed, wherein said fluid dispensing container comprises a reducible volume;
   (b.) a movable portion slidably disposed within said fluid dispensing container, said movable portion being capable of automatically adjusting in response to changes in fluid volume due to differential thermal expansion and/or contraction of said fluid contained within said fluid dispensing container, wherein said movable portion and said fluid dispensing container define a net fluid volume that changes as said movable portion moves with respect to said fluid dispensing container, and wherein an interference fit of said movable portion and said fluid dispensing container creates a friction force wherein the differential thermal expansion and/or contraction force is greater than the friction force of said fluid dispensing container;
   (c.) a metering drive that selectively contacts said movable portion, wherein said metering drive comprises an engaged position wherein said metering drive is in contact with said movable portion of said fluid dispensing container and a disengaged position wherein said metering drive is not in contact with said movable portion of said fluid dispensing container, wherein said engaged position is used as a starting point for incremental movement of the metering drive for delivering a specific quantity of fluid, said starting point comprising a point wherein said metering drive is re-zeroed;
   (d.) a sensor that senses when said metering drive contacts said movable portion;
   wherein said metering drive is actuated a known amount from said starting point thus moving said movable portion and reducing said reducible volume of said fluid dispensing container and causing the specific quantity of said fluid to be dispensed from said fluid dispensing container;
   wherein said specific quantity of said fluid from said fluid dispensing container further comprises a dose, wherein said fluid dispensing container comprises more than one dose, and;
   wherein said metering device is capable of delivering more than one substantially accurate and substantially reproducible dose.

2. The metering device of claim 1, wherein said starting point comprising a point wherein said metering drive engages said movable portion of said fluid dispensing container.

3. The metering device of claim 1, wherein said starting point comprises a point when fluid delivery commences.

4. The metering device of claim 1, wherein said starting point comprises a point when said fluid dispensing container is primed.

5. The metering device of claim 1, wherein said starting point comprises a point wherein said metering drive becomes fully loaded.

6. The metering device of claim 1, further comprising a sliding force, wherein said sliding force is a force required to ensure that said plunger moves before a cracking pressure of an outlet valve during differential thermal expansion and a force required to ensure that the plunger moves with ambient atmospheric pressure during differential thermal contraction.

7. The metering device of claim 1, further comprising an expansion sliding force, wherein said expansion sliding force is a force low enough to ensure that said movable portion moves before leakage from an outlet during differential thermal expansion.

8. The metering device of claim 1, further comprising a contraction sliding force, wherein said contraction sliding force is a force low enough to ensure that said movable portion moves with ambient atmospheric pressure during differential thermal contraction.

9. The metering device of claim 1, wherein said movable portion of said fluid dispensing container moves relative to said fluid dispensing container in response to an expansion of said net fluid volume in said fluid dispensing container caused by a change in temperature and/or moves relative to said fluid dispensing container in response to a contraction of said net fluid volume in said fluid dispensing container cause by an opposite change in temperature.

10. The metering device of claim 1, wherein said metering drive further comprises:
a motor;
an output shaft of said motor;
a gear train coupled to said output shaft; and
a lead screw coupled to said gear train, wherein said lead screw selectively contacts said movable portion of said fluid dispensing container.

11. The metering device of claim 10, wherein said metering drive can be backed off of and disengaged from said movable portion of said fluid dispensing container.

12. The metering device of claim 11, wherein said motor further comprises:
a reversible motor;
wherein said motor is run in a forward direction to cause said metering drive to engage and push said movable portion of said fluid dispensing container forward to reduce said net fluid volume; and
wherein said motor is run in a reverse direction to back said metering drive off of said movable portion of said fluid dispensing container.

13. The metering device of claim 11, wherein said metering drive is backed off a distance sufficient to allow said movable portion of said fluid dispensing container to expand through a pre-determined temperature range that said metering device is expected to operate in.

14. The metering device of claim 10, wherein said metering drive can be advanced at multiple and/or variable speeds.

15. The metering device of claim 14, further comprising:
a seeking speed and a delivery speed;
wherein said metering drive is advanced at said seeking speed toward said movable portion of said fluid dispensing container until said metering drive contacts said movable portion; and
wherein said metering drive is advanced at said delivery speed after said metering drive contacts said movable portion of said fluid dispensing container.

16. The metering device of claim 15, wherein said motor further comprises a multiple and/or variable speed motor.

17. The metering device of claim 1, wherein said sensor further comprises a switch type sensor.

18. The metering device of claim 1, wherein said sensor further comprises an electric circuit and algorithm that monitors a current of a motor that drives said metering drive, wherein said starting point is determined to be a point when the motor becomes loaded.

19. The metering device of claim 1, wherein said specific quantity of said fluid from said fluid dispensing container further comprises a set volume of said fluid.

20. The metering device of claim 1, further comprising:
an outlet opening in said fluid dispensing container for allowing fluid to exit said fluid dispensing container; and
a valve in fluid communication with said outlet opening, wherein said valve prevents fluid from exiting said fluid dispensing container until sufficient force is applied to said movable portion of said fluid dispensing container to overcome a closing force on said valve.

21. The metering device of claim 20, wherein a force required to move said movable portion of said fluid dispensing container in response to differential thermal expansion is less than said opening force on said valve.

22. The metering device of claim 1, wherein a force required to move said movable portion of said fluid dispensing container in response to differential thermal contraction is less than available atmospheric pressure.

23. The metering device of claim 20, further comprising:
a fluid passageway in fluid communication with said outlet opening of said fluid dispensing container; and
a nozzle in fluid communication with said fluid passageway, wherein said nozzle dispenses said fluid as an aerosol.

24. The metering device of claim 1, further comprising:
a seal between said movable portion of said fluid dispensing container and a rigid portion of said fluid dispensing container;
wherein said seal allows said movable portion of said fluid dispensing container to move relative to said rigid portion of said fluid dispensing container, wherein said seal substantially prevents the ingress of contaminants into said fluid dispensing container and/or the egress of fluid out of said fluid dispensing container at an interface between said fluid dispensing container and said movable portion.

25. The metering device of claim 1, wherein said metering drive further comprises:
a gear having a plurality of teeth and an axis of rotation;
a lead screw extending from one side of said gear along said axis of rotation, wherein said lead screw is threadedly engaged with a mating thread fixed from rotation on said gear; and wherein said rotation of said gear causes axial movement of said lead screw.

26. The metering device of claim 25, further comprising:
an encoder disk driven by said gear to measure a movement of said metering drive; a plurality of windows disposed annularly around said encoder disk.

27. The metering device of claim 26, further comprising:
a sensor for sensing a rotation of said encoder disk by monitoring said plurality of windows;
wherein each of said plurality of windows represents a set volume of said fluid.

28. The metering device of claim 1, wherein said metering system further comprises a syringe-based metering system, and wherein:
said fluid dispensing container further comprises a syringe;
said movable portion further comprises a piston plunger slidably disposed within said syringe; and
said metering drive further comprises a lead screw;
wherein said lead screw allows said plunger to move axially within said syringe in response to differential thermal expansion and/or contract between said syringe and said fluid within said syringe when the metering device is not in use; and
wherein said lead screw locates an axial position of said plunger within said syringe before dispensing said fluid from said syringe.

29. The metering device of claim 1, wherein said fluid in said fluid dispensing container further comprises a drug formulated in ethanol solution.

30. The metering device of claim 1, further comprising a motor, wherein said metering drive is coupled to said motor;
said metering drive further comprising a mating surface and tip geometry;
said movable portion further comprising a mating surface and shape that correspond to the mating surface and tip geometry of said metering drive; and
wherein said mating surfaces and tip geometry facilitate sensing of said metering drive contacting and engaging said movable portion by amplifying a change in motor current of said motor.

31. The metering device of claim 30, said metering drive further comprises a lead screw, said mating surface and tip geometry at a distal end of said lead screw further comprises:

a cylindrical portion; a tapered shoulder; said movable portion further comprising a plunger, said mating surface and shape at a rear end of said plunger further comprises:
- an opening for receiving said cylindrical portion of said lead screw; and
- a tapered surface that contacts said tapered shoulder of said lead screw;
- wherein said cylindrical portion and said opening provide a piloting function to ensure good contact and said tapered shoulder and said tapered surface form a friction contact between said lead screw and said plunger.

32. A syringe-based metering system that mitigates differential thermal expansion and/or contraction, said syringe-based metering system comprising:
- (a.) a syringe defining an interior volume for containing a fluid;
- (b.) an outlet opening at a front end of said syringe;
- (c.) a piston-type plunger slidably disposed within said syringe through an opening in a rear end of said syringe and having an interference fit that creates a friction force between said piston-type plunger and said syringe wherein the differential thermal expansion and/or contraction force is greater than the friction force of said syringe, said piston-type plunger being slidably disposed within said syringe and capable of automatically adjusting in response to changes in fluid volume due to differential thermal expansion and/or contraction of said fluid contained within said syringe;
- (d.) a net fluid volume defined by a location of said plunger within said syringe, wherein said net fluid volume changes with movement of said plunger within said syringe; and
- (e.) a metering drive that selectively engages and disengages said plunger, wherein said metering drive engages said plunger through said opening in said rear end of said syringe to arrive at an engaged position, wherein said engaged position is capable of being used as a starting point for incremental movement of the metering drive, wherein said metering drive is advanced to expel a specific quantity of fluid from said syringe, wherein said specific quantity of said fluid from said fluid dispensing container further comprises a dose, wherein said fluid dispensing container comprises more than one dose, and wherein said metering device is capable of delivering substantially accurate and substantially reproducible doses; and wherein said metering drive disengages said plunger by being backed off of said plunger when said syringe-based metering system is not in use; and
- (f.) a sensor that senses when said metering drive contacts said movable portion.

33. The syringe-based metering system of claim 32, wherein said metering drive further comprises an operating and a non-operating position;
- wherein said metering drive is not in contact with said plunger when said syringe-based metering system is not operating;
- wherein said metering drive seeks and locates said plunger when said syringe-based metering system is activated; and
- wherein said metering drive is in contact with and pushes said plunger forward into said syringe when said syringe-based metering system is operating, wherein said net fluid volume is reduced as said metering drive moves said plunger into said syringe and fluid is expelled through said outlet opening.

34. The syringe-based metering system of claim 32, further comprising:
- a clearance between said metering drive and said plunger when said syringe-based metering system is not operating;
- wherein said clearance allows said plunger to slide rearward in said syringe in response to differential thermal expansion between said syringe and said fluid contained within said syringe.

35. The syringe-based metering system of claim 32, further comprising:
- a valve in fluid communication with said outlet opening of said syringe; and a differential thermal expansion sliding force, wherein said differential thermal expansion sliding force is the force required to cause said plunger to slide rearward in response to differential thermal expansion resulting from an increase in temperature;
- wherein said differential thermal expansion sliding force is less than a cracking pressure of said valve.

36. The syringe-based metering system of claim 35, wherein said valve substantially prevents leakage of fluid from said syringe until said metering drive is activated and pushes said plunger forward a sufficient distance to force said fluid out of said syringe into said valve and overcome said cracking pressure of said valve.

37. The syringe-based metering system of claim 32, further comprising:
- a differential thermal contraction sliding force, wherein said differential thermal contraction sliding force is the force required to cause said plunger to slide forward in response to differential thermal contraction resulting from a decrease in temperature.

38. The syringe-based metering system of claim 37, wherein said differential thermal contraction sliding force is less than available atmospheric pressure.

39. The syringe-based metering system of claim 32, further comprising:
- an interference fit between said syringe and said plunger;
- an actuation sliding force, wherein said actuation sliding force is the force required to overcome a friction force of said interference fit between said syringe and said plunger, and wherein said actuation sliding force causes said plunger to slide forward in to said syringe; and
- wherein said actuation sliding force is equal to a force required to overcome friction between said plunger and an inner wall of said syringe plus a resistive force on said plunger created by a pressure of said fluid in said syringe.

40. The syringe-based metering system of claim 32, further comprising:
- a seal formed between said syringe and said plunger,
- wherein said seal substantially prevents fluid from leaking out of an interior of said syringe between said syringe and said plunger, and
- wherein said plunger and seal seals said fluid within said syringe.

41. The syringe-based metering system of claim 40, further comprising a sealing force, wherein:
- said sealing force is the force required to substantially prevent said fluid from leaking between said syringe and said plunger, and
- wherein said sealing force multiplied by a coefficient of friction for a given material pair is less than an actuation sliding force exerted by said metering drive to push said plunger forward.

42. The syringe-based metering system of claim 40, further comprising a sealing force, wherein:
said sealing force is the force required to substantially prevent said fluid from leaking between said syringe and said plunger,
said sealing force multiplied by a coefficient of friction for a given material pair is less than a differential thermal expansion sliding force, which is the force required to cause said plunger to slide rearward in response to differential thermal expansion resulting from an increase in temperature; and
said sealing force multiplied by a coefficient of friction for a given material pair is less than a differential thermal contraction sliding force, wherein said differential thermal contraction sliding force is the force required to cause said plunger to slide forward in response to differential thermal contraction resulting from a decrease in temperature.

43. A method of mitigating the effects of differential thermal expansion in a metering system to ensure accurate metering of a fluid, said method comprising:
containing a fluid to be dispensed in a fluid dispensing container having a reducible volume;
providing a movable portion that can slide within said fluid dispensing container to reduce said reducible volume causing said fluid to be dispensed, wherein an interference fit between said movable portion and said fluid dispensing container creates a friction force between said movable portion and said fluid dispensing container;
providing a metering drive having an engaged position and a disengaged position, wherein in the engaged position, said metering drive can selectively engage said movable portion to move said movable portion causing said reducible volume of said fluid dispensing container to be reduced in an operating mode and wherein said engaged position is capable of being used as a starting point for incremental movement of the metering drive for delivering a specific quantity of fluid; wherein said metering system has a differential thermal expansion sliding force such that said movable portion is capable of automatically sliding rearward within said fluid dispensing container in response to an increasing temperature, and wherein said metering system has a differential thermal contraction sliding force such that said movable portion is capable of automatically sliding forward within said fluid dispensing container in response to a decreasing temperature, wherein said differential thermal contraction sliding force is greater than said friction force;
mitigating the effects of differential thermal expansion and/or contraction by allowing said metering drive to be backed off of said movable portion in a non-operating mode to provide a clearance between said movable portion and said metering drive and by allowing said movable portion to automatically move back and forth in response to an expanding and/or contracting fluid volume of said fluid contained within said fluid dispensing container caused by an increasing and/or decreasing temperature; and
metering a specific quantity of fluid by incremental movement from said starting point, wherein said specific quantity of said fluid from said fluid dispensing container further comprises a dose, wherein said fluid dispensing container comprises more than one dose, and wherein said metering device is capable of delivering substantially accurate and substantially reproducible doses;
wherein in the disengaged position, said metering drive is not in contact with said movable portion of said fluid dispensing container;
wherein said metering system further comprises a sensor that senses when said metering drive contacts said movable portion.

44. The method of claim 43, said method further comprising:
mitigating the effect of differential thermal expansion and/or contraction between said fluid dispensing container and said fluid contained within said fluid dispensing container by allowing said movable portion to move back and forth in response to an expanding and/or contracting fluid volume of said fluid contained within said fluid dispensing container caused by an increasing and/or decreasing temperature.

45. The method of claim 43, said method further comprising:
mitigating the effect of differential thermal contraction between said fluid dispensing container and said fluid contained within said fluid dispensing container by allowing said movable portion to move forward in response to a contracting fluid volume of said fluid contained within said fluid dispensing container caused by a decreasing temperature.

46. The method of claim 43, said method further comprising:
mitigating the effect of differential thermal expansion between said fluid dispensing container and said fluid contained within said fluid dispensing container by allowing said movable portion to move backward in response to a expanding fluid volume of said fluid contained within said fluid dispensing container caused by an increasing temperature.

47. The method of claim 43, said method further comprising:
filling a nozzle dead volume with fluid during said step of seeking and before designation of said starting point.

48. The method of claim 43, said method further comprising:
sensing a movement of said metering drive; and
correlating said movement of said metering drive to said set volume of fluid to deliver a set volume of fluid from said fluid dispensing container.

49. The method of claim 48, said step of sensing a movement of said metering drive further comprises:
engaging an encoder disk with a gear train driving said metering drive; and counting one or more windows in said encoder disk, wherein each of said one or more windows represents a set volume of fluid.

50. The method of claim 43, said method further comprising:
providing an interference fit between said movable portion and said fluid dispensing container, wherein said interference fit creates a friction force between said movable portion and said fluid dispensing container;
designing said metering system to have a differential thermal expansion sliding force required to cause said movable portion to slide rearward within said fluid dispensing container in response to an increasing temperature, wherein said differential thermal expansion sliding force is greater than said friction force between said movable portion and said fluid dispensing container;
designing said metering system to have a differential thermal contraction sliding force required to cause said movable portion to slide forward within said fluid dispensing container in response to a decreasing temperature, wherein said differential thermal contraction sliding force is greater than said friction force between said movable portion and said fluid dispensing container plus a resistive force on said movable portion created by a pressure of said fluid in said fluid dispensing container acting on said movable portion.

51. The method of claim 50, said method further comprising:
   designing said metering system to have an actuation sliding force required to cause said movable portion to slide within said fluid dispensing container when said metering system is actuated, wherein said actuation sliding force is greater than said friction force between said movable portion and said fluid dispensing container plus a resistive force on said movable portion created by a pressure of said fluid in said fluid dispensing container acting on said movable portion.

52. The method of claim 50, said method further comprising:
   providing an interference fit between said movable portion and said fluid dispensing container; and
   sealing said fluid within said fluid dispensing container using said interference fit.

53. The method of claim 43, said method further comprising sealing an interface between said movable portion and said fluid dispensing container.

\* \* \* \* \*